(12) United States Patent
Kazantsev

(10) Patent No.: US 8,153,803 B2
(45) Date of Patent: Apr. 10, 2012

(54) COMPOSITIONS AND METHODS FOR MODULATING SIRTUIN ACTIVITY

(75) Inventor: Aleksey G. Kazantsev, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 525 days.

(21) Appl. No.: 12/143,478

(22) Filed: Jun. 20, 2008

(65) Prior Publication Data

US 2009/0259044 A1  Oct. 15, 2009

Related U.S. Application Data

(63) Continuation-in-part of application No. 12/100,080, filed on Apr. 9, 2008, which is a continuation of application No. 11/488,293, filed on Jul. 18, 2006.

(51) Int. Cl.
*C07D 215/38* (2006.01)
(52) U.S. Cl. ..................................................... 546/171
(58) Field of Classification Search ........................ None
See application file for complete search history.

(56) References Cited

U.S. PATENT DOCUMENTS

| | | | |
|---|---|---|---|
| 5,144,001 | A | 9/1992 | Maresca et al. |
| 5,328,470 | A | 7/1994 | Nabel |
| 5,994,392 | A | 11/1999 | Shashoua |
| 6,015,555 | A | 1/2000 | Friden |

FOREIGN PATENT DOCUMENTS

| | | |
|---|---|---|
| JP | 63054363 A | 3/1988 |
| WO | 01/46200 A1 | 6/2001 |
| WO | 2005087217 | 9/2005 |

OTHER PUBLICATIONS

Rautio et al., Prodrugs: Design and Clinical Applications, 7 Nat. Rev. Drug Dis. 255-70 (2008).*
Grozinger, C.M. et al., Proc. Natl. Acad. Sci. USA, 96:4868-4873 (1999). "Three proteins define a class of human histone deacetylases related to yeast Hda1p."
Khochbin, S. et al., Current Opinion in Genetics & Development, 11:162-166 (2001). "Functional significance of histone deacetylase diversity."
Wang, A.H. et al., Molecular and Cellular Biology, 19(11):7816-7827 (1999). "HAC4, a human histone deacetylase related to yeast HDA1, is a transcriptional corepressor."
Elderfield, R.C. and Claflin, E.F., Journal of the American Chemical Society, 74(12):2953-2959 (1952). "The Reaction of 8-Nitroquinoline with Thiophenol-Thiophenoxide Ion. An Example of Anionic Substitution.".
Kordik, C.P. et al., Bioorganic & Medicinal Chemistry Letters, 11:2287-2290 (2001). "Pyrazolecarboxamide Human Neuropeptide Y5 Receptor Ligands with in Vivo Antifeedant Activity.".
Stupnikova, T.V. et al., vol. 7:57-59 (1982); abstract CAS Reg. No. 83273-28-3. "Synthesis and Reactions of Quinolylindoles with an Azomethine Bridge Between the Ring Systems.".
International Search Report issued in PCT/US07/73803 on Nov. 3, 2008.
Chen et al., Proc. Natl. Acad. Sci. USA vol. 91 (1994) pp. 3054-3057.
Cruikshank et al., J. Acquired Immune Deficiency Syndromes and Human Retrovirology vol. 14 (1997) p. 193.
Czarnik, Curr. Opin. Bio. vol. 1 (1997) pp. 60-66.
Gaffer et al. J. Clin. Path. vol. 36 (1983) pp. 539-545.
Goldstein et al., Scientific American vol. 255 (1996) pp. 74-83.
Grozinger et al. J. Biol. Chem. vol. 276 (2001) pp. 38837-38843.
Grozinger et al. Proc. Natl. Acad. Sci. USA vol. 96 (1999) pp. 4868-4873.
Haynes et al., J. Immunol. vol. 127 (1981) pp. 347-351.
Howitz et. Nature vol. 425 (2003) pp. 191-196.
Khochbin et al. Curr. Opin. Genet. Dev. vol. 11 (2001) pp. 162-166.
McLean et al. J. Neurochem. vol. 83 (2002) pp. 846-854.
McLean et al. Neuroscience vol. 104 (2001) (2002) pp. 901-912.
North et al. Mol. Cell. vol. 11 (2003) pp. 437-444.
Omary et al. Nature vol. 286 (1980) pp. 888-891.
Pardridge et al. Endocrin Rev. vol. 7 (1996) pp. 314-330.
Rovera Blood vol. 59 (1982) pp. 671-678.
Sutherland et al. Proc. Natl. Acad. Sci. USA vol. 78 (1987) pp. 4515-4519.
Wang et al. Mol. Cell. Biol., vol. 19 (1999) pp. 7816-7827.

* cited by examiner

*Primary Examiner* — Janet Andres
*Assistant Examiner* — Timothy R Rozof
(74) *Attorney, Agent, or Firm* — Nixon Peabody LLP; David S. Resnick; Leena H. Karttunen Contarino

(57) ABSTRACT

The present invention is based, in part, on our discovery of compounds that inhibit an activity of a sirtuin (e.g., compounds that inhibit or preferentially inhibit an activity of SIRT2) and are therefore believed useful in the treatment or prevention of diseases associated with sirtuin activity. These diseases include, but are not limited to, neurological disorders such as Parkinson's Disease (PD).

9 Claims, 19 Drawing Sheets

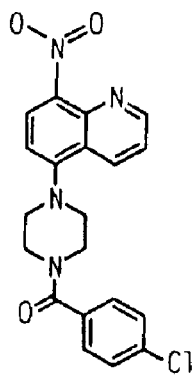
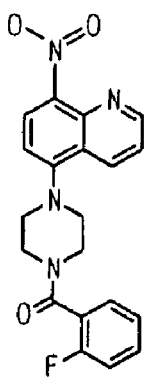
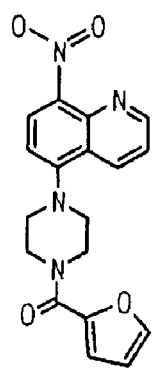
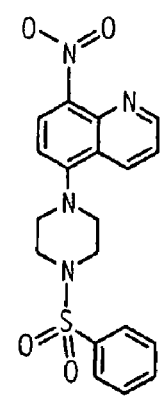
SIRT2
IC50=17.5μM
Some SIRT3, T/D
Stimulation
of Aggregation
FIG. 1A
SIRT2
IC50=20μM
Weak Stimulation
of Aggregation
FIG. 1B
55% SIRT2
at 25μM
FIG. 1C
SIRT2
IC50=15μM
FIG. 1D
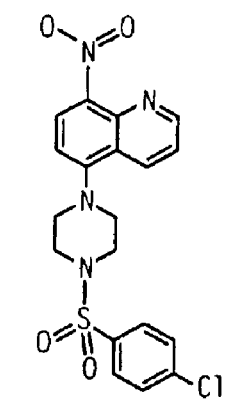
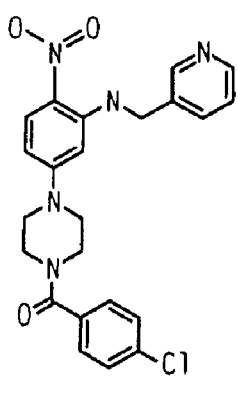
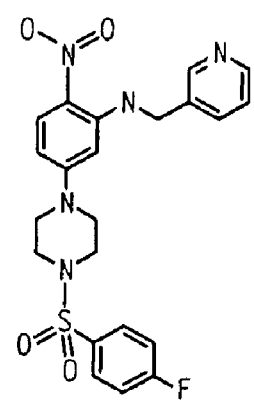
SIRT2
IC50=20μM
FIG. 1E
SIRT2 IC50=20μM
SIRT3 IC50=25μM
No Effect on
Aggregation
FIG. 1F
Activity Weak,
IC50 N/D
No Effect on
Aggregation
FIG. 1G

SIRT2
IC50=25μM

SIRT2 IC50=20μM
SIRT3 IC50=20μM
No Effect on
Aggregation

SIRT2
IC50=25μM
No Effect on
Aggregation

SIRT2
IC50=14μM
Some SIRT3, T/D
No Effect on
PolyQ Aggregation,
Inhibitor of a-syn.
Aggregation SIRT2
IC50=8.5μM
No Effect on
Aggregation SIRT2
IC50=7.5μM
No Effect on
Aggregation At 10μM
25% SIRT2
85% SIRT3

Aggregation Inhibitor

At 10μM
50% SIRT2
85% SIRT3

Aggregation Inhibitor

At 10μM
50% SIRT2
85% SIRT3

Aggregation Inhibitor

% of SIRT2 Activity Remains in Presence of 10μM Compound in Enzymatic Assay

80% SIRT2
at 10μM

75% SIRT2
at 10μM

70% SIRT2
at 10μM

80% SIRT2
at 10μM

70% SIRT2
at 10μM

100% SIRT2
at 10μM

100% SIRT2
at 10μM

75% SIRT2
at 10μM

85% SIRT2
at 10μM

50% SIRT2
at 10μM

45% SIRT2
at 10μM

65% SIRT2
at 10μM

70% SIRT2
at 10μM

70% SIRT2
at 10μM

85% SIRT2
at 10μM

70% SIRT2
at 10μM

60% SIRT2
at 10μM

75% SIRT2
at 10μM

100% SIRT2
at 10μM

60% SIRT2
at 10μM

50% SIRT2
at 10μM

50% SIRT2
at 10μM

45% SIRT2
at 10μM

50% SIRT2
at 10μM

SIRT2
IC50=8μM

No Effect on
Aggregation

SIRT2
IC50=8μM

No Effect on
Aggregation

SIRT2
IC50=8μM,
SIRT3
IC50= μM
No Effect on
Aggregation

SIRT2
IC50=8μM

At 10μM
65% SIRT2
75% SIRT3
No Effect on
Aggregation

At 10μM
65% SIRT2
65% SIRT3
No Effect on
Aggregation

At 10μM
55% SIRT2
80% SIRT3

At 10μM
75% SIRT2
100% SIRT3

At 10μM
55% SIRT2
100% SIRT3

At 10μM
100% SIRT2
100% SIRT3

SIRT2
IC50=8μM
At 10μM
SIRT3 75%

Effect on Aggregation
to be Determine

At 10μM
30% SIRT2
100% SIRT3

Aggregation
Inhibitor

At 10μM
28% SIRT2
100% SIRT3
Aggregation
Inhibitor

At 10μM
30% SIRT2
100% SIRT3
Aggregation
Inhibitor

At 10μM
70% SIRT2
100% SIRT3
Weak
Aggregation
Inhibitor

At 10μM
100% SIRT2
100% SIRT3
No Effect on
Aggregation

At 10μM
85% SIRT2
95% SIRT3
No Effect on
Aggregation

At 10μM
100% SIRT2
100% SIRT3
No Effect on
Aggregation

At 10μM
100% SIRT2
100% SIRT3
No Effect on
Aggregation

At 10μM
100% SIRT2
100% SIRT3
No Effect on
Aggregation

B5-9

| At 25μM 60% SIRT2 | At 25μM | At 25μM SIRT2 75% | At 25μM SIRT2 100% |

Aggregation Inhibitor (FIG. 1I')

Aggregation Stimulator (FIG. 1J')

At 25μM SIRT2 50%
At 10μM SIRT2 75%
FIG. 1M'

At 10μM SIRT2 70%
Aggregation Inhibitor
FIG. 1N'

At 10μM SIRT2 75%
FIG. 1O'

At 10μM SIRT2 75%
FIG. 1P'

At 10μM
SIRT2 80%

At 10μM
SIRT2 65%

Aggregation
Inhibitor

At 10μM
SIRT2 100%

At 10μM
SIRT2 85%

At 10μM
SIRT2 100%

At 10μM
SIRT2 100%

SIRT2
IC50=11μM

Aggregation
Inhibitor

At 10μM
SIRT2 50%

Aggregation
Inhibitor

At 10μM
SIRT2 75%

Weak
Aggregation
Inhibitor

At 10μM
SIRT2 68%

Aggregation
Inhibitor

At 10μM
SIRT2 60%

Aggregation
Inhibitor

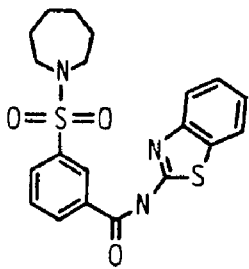 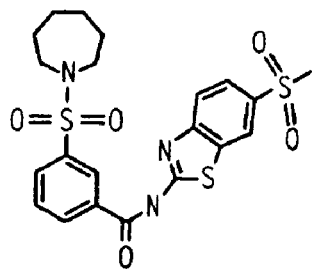 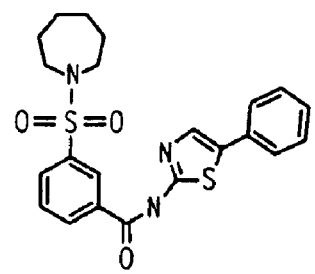
FIG. 2J　　　　　FIG. 2K　　　　　FIG. 2L
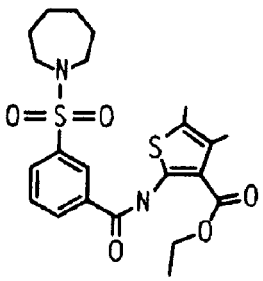 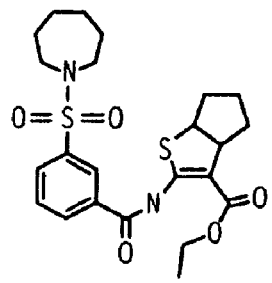 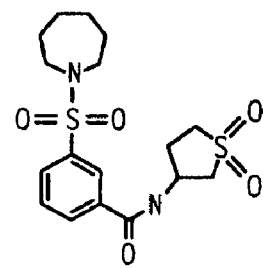
FIG. 2M　　　　　FIG. 2N　　　　　FIG. 2O
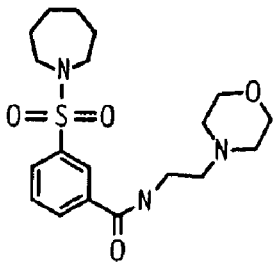 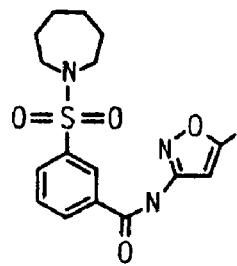 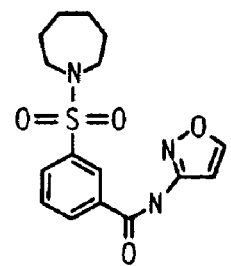
FIG. 2P　　　　　FIG. 2Q　　　　　FIG. 2R
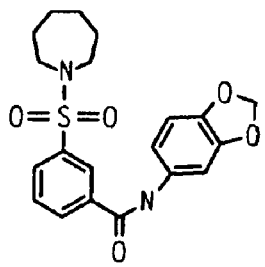 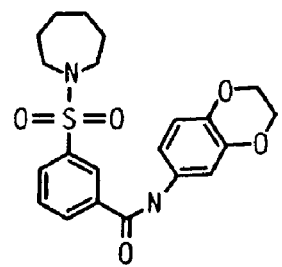 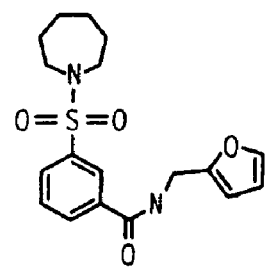
FIG. 2S　　　　　FIG. 2T　　　　　FIG. 2U Aggregation Inhibitor Aggregation Inhibitor Weak Aggregation Inhibitor Aggregation Inhibitor Aggregation Inhibitor Aggregation Inhibitor Weak Aggregation Inhibitor At 10μM
SIRT2 60%

At 10μM
SIRT2 70%

| AGK Scaffold | 1 | 2 | 3 | 4 | 5 | 6 | 7 | 8 |
|---|---|---|---|---|---|---|---|---|
| SIRT1 IC50 (μM) | >50 | >50 | >50 | >50 | >50 | >50 | >50 | >50 |
| SIRT2 IC50 (μM) | 5.5 | 3.5 | >10 | 6 | >50 | >50 | >50 | >50 |
| SIRT3 IC50 (μM) | >50 | >50 | >50 | >50 | >50 | >50 | >50 | >50 |
FIG. 5D
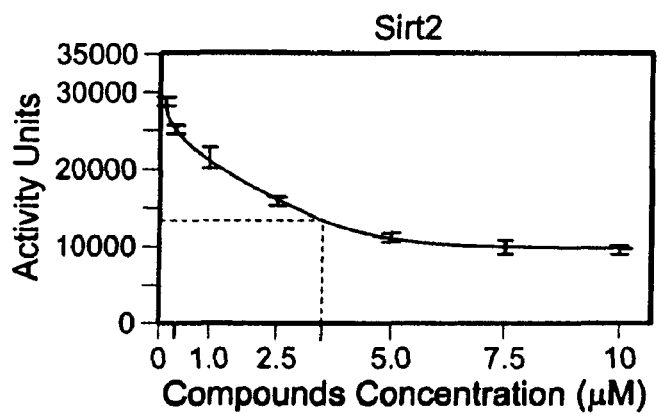
FIG. 5E
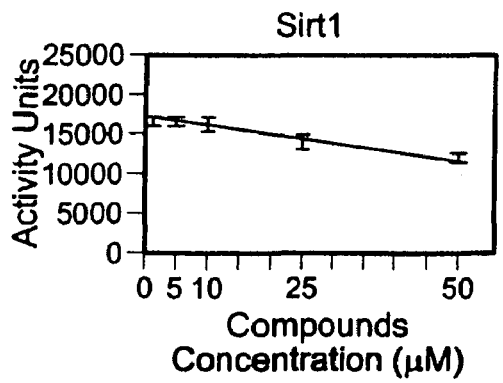
FIG. 5F
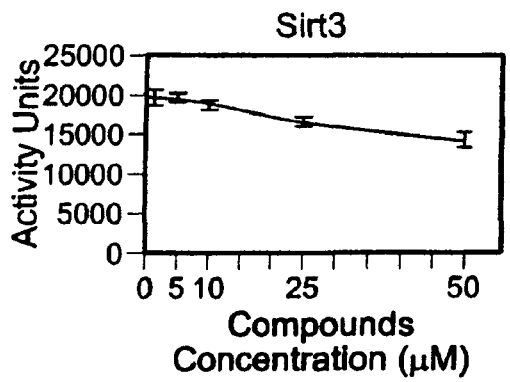
FIG. 5G

```
HOMO SAPIENS SIRT1
1   migtdprtil kdllpetipp pelddmtlwq ivinilsepp krkkrkdint iedavkllqe
61  ckkiivltga gvsvscgipd frsrdgiyar lavdfpdlpd pqamfdieyf rkdprpffkf
121 akeiypgqfq pslchkfial sdkegkllrn ytqnidtleq vagiqriiqc hgsfatascl
181 ickykvdcea vrgalfsqvv prcprdpade plaimkpeiv ffgenlpeqf hramkydkde
241 vdllivigss lkvrpvalip ssiphevpqi linreplphl hfdvellgdc dviinelchr
301 lggeyaklcc npvklseite kpprtqkela ylselpptpl hvsedssspe rtsppdssvi
361 vtlldqaaks nddldvsesk gcmeekpqev qtsrnvesia eqmenpdlkn vgsstgekne
421 rtsvagtvrk cwpnrvakeq isrrldgnqy lflppnryif hgaevysdse ddvlsssscg
481 snsdsgtcqs psleepmede seieefyngl edepdvpera ggagfgtdgd dqeaineais
541 vkqevtdmny psnks HOMO SAPIENS SIRT2
1   mdflrnlfsq tlslgsqker lldeltlegv arymqsercr rviclvgagi stsagipdfr
61  spstglydnl ekyhlpypea ifeisyfkkh pepffalake lypgqfkpti chyfmrllkd
121 kglllrcytq nidtleriag leqedlveah gtfytshcvs ascrheypls wmkekifsev
181 tpkcedcqsl vkpdivffge slparffscm qsdflkvdll lvmgtslqvq pfasliskap
241 lstprllink ekagqsdpfl gmimglgggm dfdskkayrd vawlgecdqg clalaellgw
301 kkeledlvrr ehasidaqsg agvpnpstsa spkkspppak deartterek pq HOMO SAPIENS SIRT3
1   mafwgwraaa alrlwgrvve rveagggvgp fqacgcrlvl ggrddvsagl rgshgargep
61  ldparplqrp prpevprafr rqpraaapsf ffssikggrr sisfsvgass vvgsggssdk
121 gklslqdvae liraracqrv vvmvgagist psgipdfrsp gsglysnlqq ydlpypeaif
181 elpfffhnpk pfftlakely pgnykpnvth yfirllhdkg lllrlytqni dglervsgip
241 asklveahgt fasatctvcq rpfpgedira dvmadrvprc pvctgvvkpd ivffgeplpq
301 rfllhvvdfp madlllilgt slevepfasl teavrssvpr llinrdlvgp lawhprsrdv
361 aqlgdvvhgv eslvellgwt eemrdlvqre tgkldgpdk
```

FIG. 8

COMPOSITIONS AND METHODS FOR MODULATING SIRTUIN ACTIVITY

CROSS-REFERENCE TO RELATED APPLICATIONS

This application is a continuation-in-part application of a copending U.S. application Ser. No. 12/100,080, filed Apr. 9, 2008, which is a continuation application under 35 U.S.C. §120 of U.S. application Ser. No. 11/488,293, filed Jul. 18,2006, now abandoned, which is herein incorporated by reference in its entirety.

TECHNICAL FIELD

This invention relates to compositions and methods for modulating the activity of a sirtuin. We describe exemplary compounds, which may be contained in pharmaceutical compositions, the screening methods by which they were discovered, and their use as therapeutic or prophylactic agents.

BACKGROUND

Gene expression is regulated by complex interactions between proteins such as transcription factors and genetic material. Factors that influence the process include DNA methylation, ATP-dependent chromatin remodeling, and modification of histones by dynamic acetylation and deacetylation of ε-amino groups on certain lysine residues (Wang et al., *Mol. Cell. Biol.,* 19:7816-7827, 1999). The enzymes responsible for reversible acetylation and deacetylation processes are histone acetyltransferases (HATs) and histone deacetylases (HDACs or HDAcs), respectively (Grozinger et al, *Proc. Natl. Acad. Sci. USA,* 96:4868-4873, 1999).

Mammalian HDACs have been categorized based on sequence similarity (see, for example, Khochbin et al., *Curr. Opin. Genet Dev.* 11:162-166, 2001) and it is the Class III HlDAcs that include the yeast Sir2-like proteins and other sirtuins. Sirtuins are NAD-dependent deacetylases, which distinguishes them from other HDAcs. The yeast Sir2 protein was among the first sirtuins studied, and it was determined to play a role in mating switch silencing. Later, in yeast, fly and worm models, Sir2 was shown to influence the aging process and promote longevity.

Humans have seven distinct sirtuin gene products, which are localized in the nucleus, cytoplasm, and mitochondria, and are thought to play important and diverse regulatory roles in specialized mammalian cells. The mammalian correlate of the yeast Sir2 protein is SIRT1. Activation of SIRT1 with the small molecule resveratrol prolonged the lifespan of flies and wors. Human sirtuin 2 (SIRT2) is localized to the cytoplasm and has been implicated in the process of cell division via deacetylation of α-tubulin, a well-known SIRT2 substrate. Other substrates may include the transcription factor p53 and histone H3/H4. Human sirtuin 3 (SIRT3) and human sirtuin 4 (SIRT4) are mitochondrial proteins that are not yet well understood. The substrates for these enzymes have yet to be identified. Even less is currently known about SIRT5 and SIRT6.

SUMMARY

The present invention is based, in part, on our discovery of compounds that inhibit an activity of a sirtuin (e.g., compounds that inhibit or preferentially inhibit an activity of SIRT2) and are therefore believed useful in the treatment or prevention of diseases associated with sirtuin activity. These diseases include, but are not limited to, neurological disorders, such as Parkinson's Disease (PD). Other diseases or disorders and patients amenable to treatment are described further below. The compounds were identified in our screening assays based on their ability to inhibit sirtuin activity. While these compounds may inhibit sirtuin activity by directly interacting with (e.g., binding to) a sirtuin (e.g., SIRT2), the invention is not limited to compounds that exert their effect on a disease process by any single or particular mechanism. While we tend to use the term "compound(s)", we may also use terms like "agent(s)" to refer to the molecules described herein.

We have placed each of the compounds we identified into one of three categories, which are represented by Formulas I-X, respectively. The invention encompasses these compounds in, for example, a substantially pure form, as well as various compositions containing one or more of them (e.g., concentrated stocks in various forms (e.g., powdered or freeze-dried forms), pharmaceutical formulations and kits) and methods of using them in, for example, assays (e.g., in cell-based assays or in tissue or organ culture), in animal models of disease, and in vivo to treat or prevent a disease associated with sirtuin activity and/or described herein.

Formula I is:

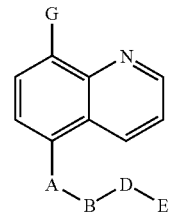

Referring to Formula I, A can be absent, S, $NR^1$, $NR^2C(S)NR^3$, or heterocycloalkyl optionally substituted with 1, 2, 3, 4, or 5 halo, OH, CN, or $C_{1-6}$ alkyl (preferably 1 or 2);

B can be absent, $C_{1-6}$ alkylenyl, $C_{2-6}$ alkenylenyl, $C_{2-6}$ alkynylenyl, —($C_{1-6}$ alkyl)-O—, aryl, heteroaryl, or $S(O)_2$, wherein said $C_{1-6}$ alkylenyl, $C_{2-6}$ alkenylenyl, $C_{2-6}$ alkynylenyl, —($C_{1-6}$ alkyl)-O—, aryl, or heteroaryl is optionally substituted with 1, 2, 3, or 4 oxo, CN, OH, halo, aryl, or heteroaryl (preferably 1 or 2);

D can be absent, $C_{1-6}$ alkylenyl, $C_{2-6}$ alkenylenyl, $C_{2-6}$ alkynylenyl, O—$C_{1-6}$ alkylenyl, aryl, heteroaryl, or heterocycloalkyl, wherein said $C_{1-6}$ alkylenyl, $C_{2-6}$ alkenylenyl, $C_{2-6}$ alkynylenyl, O—$C_{1-6}$ alkylenyl, aryl, heteroaryl, or heterocycloalkyl is optionally substituted with 1, 2, or 3 $C_{1-6}$alkyl, halo, OH, aryl, or heteroaryl (preferably 1 or 2);

E can be H, $OR^6$, aryl, heteroaryl, aryloxy, or —NHC(O)aryl, wherein said aryl, heteroaryl, aryloxy, or —NHC(O)aryl, is optionally substituted with 1, 2, 3, 4, or 5 halo, OH, alkoxy, CN, $C_{1-6}$ alkyl, amino, alkylamino, dialkylamino, or heterocyclyl (preferably 1 or 2);

G can be H, $NR^4R^5$, or $NO_2$;

$R^1$, $R^2$, and $R^3$ can each be, independently, H, $C_{1-6}$ alkyl, or $C_{1-6}$ haloalkyl;

$R^4$ and $R^5$ can each be, independently, H, C alkyl, or $C_{1-6}$ haloalkyl;

And $R^6$ can be H or $C_{1-10}$ alkyl.

Under physiological conditions (e.g. in vivo), compounds of Formula I can inhibit an activity of a sirtuin (e.g., SIRT2). In some embodiments, a compound of Formula I has an $IC_{50}$ of less than about 50 mM (e.g., less than about 25 µM, less than about 10 µM, less than about 5 µM, less than about 1 µM, or less than about 0.5 µM).

In various embodiments, A can be $NR^1$. When A is $NR^1$, $R^1$ can be H. Alternatively, or in addition, G can be H and/or B can be $C_3$ alkenylenyl. Where an alkenylenyl is substituted, the substitution can be with oxo. Where an alkenylenyl (e.g., $C_3$ alkenylenyl) is present (e.g., at the position represented by B), the alkenylenyl can be further substituted with CN. In any of the compounds described herein by Formula I, D can be heteroaryl, which can include O. In any of the compounds described herein by Formula I, E can be aryl, and the aryl can be substituted with at least one halo (e.g., two halo). For example, the halo can be at least one (e.g., two) of chloro/chlorine, fluoro/fluorine, bromo/bromine or iodo/iodine.

In some embodiments, A is NH and B is $C_{1-6}$ alkylenyl or optionally substituted with oxo. In some embodiments, D is absent and E is aryloxy, —NHC(O)aryl, wherein the aryl is optionally substituted.

In some embodiments, A is a heterocycloalkyl, e.g., a nitrogen-containing heterocyclyl such as piperidine or piperazine.

In some embodiments, G is nitro ($NO_2$).

In some embodiments, the compound has the Formula Ia

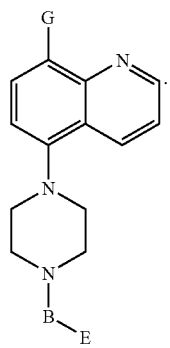

Formula Ia

In some embodiments, G is nitro ($NO_2$). In some embodiments, B is C(O) (i.e. a $C_1$ alkylenyl substituted with oxo) or $S(O)_2$. In some embodiments, E is an optionally substituted aryl or heteroaryl.

In some embodiments, the compound has the Formula Ib

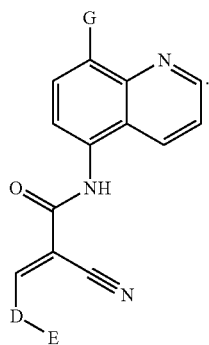

Formula (Ib)

In some embodiments, G is H. In some embodiments, D is heteroaryl (e.g., furanyl) and E is optionally substituted aryl.

A substantially pure compound that conforms to Formula I and that is within the scope of the present invention is a compound of the formula:

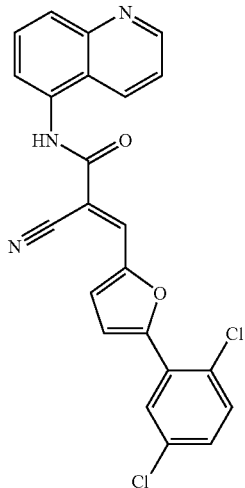

The invention encompasses pharmaceutical compositions that include compounds (e.g., substantially pure compounds) that conform to Formula I (e.g., the compound shown above) or to the other formulas described herein.

In other embodiments, the compounds (e.g., substantially pure compounds) can be compounds of Formula I in which G is $NO_2$. Alternatively, or in addition, B can be heteroaryl (e.g., a heteroaryl that includes N). The heteroaryl can be substituted with aryl (e.g., phenyl). In these embodiments and others, D can be O—$C_1$ alkylenyl and/or E can be aryl (e.g., phenyl).

For example, a compound within the scope of the invention is:

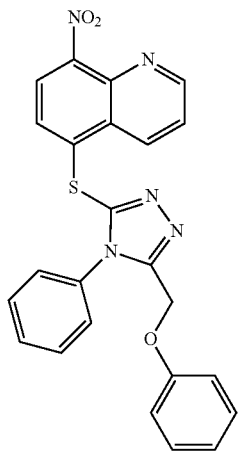

Accordingly, in a compound conforming to Formula I, A is S. Alternatively, or in addition, in a compound conforming to Formula I, one or more of the following requirements is satisfied: G is $NO_2$; B is heteroaryl (e.g., a heteroaryl comprising N or a heteroaryl substituted with aryl (e.g., phenyl)); D is O—$C_1$ alkylenyl; and E is aryl (e.g., phenyl).

Formula II is:

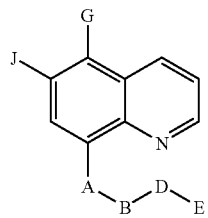

Referring to Formula II, A can be absent, S, $NR^1$, $NR^2C(S)NR^3$, or heterocycloalkyl optionally substituted with 1, 2, 3, 4, or 5 halo, OH, CN, or $C_{1-6}$ alkyl (preferably 1 or 2);

B can be absent, $C_{1-6}$ alkylenyl, $C_{2-6}$ alkenylenyl, $C_{2-6}$ alkynylenyl, —($C_{1-6}$ alkyl)-O—, aryl, heteroaryl or $S(O)_2$, and the $C_{1-6}$ alkylenyl, $C_{2-6}$ alkenylenyl, $C_{2-6}$ alkynylenyl, —($C_{1-6}$ alkyl)-O—, aryl, or heteroaryl can be optionally substituted with 1, 2, 3, or 4 oxo, CN, OH, halo, aryl or heteroaryl (preferably 1 or 2);

D can be absent, $C_{1-6}$ alkylenyl, $C_{2-6}$ alkenylenyl, $C_{2-6}$ alkynylenyl, O—$C_{1-6}$ alkylenyl, aryl, heteroaryl, or heterocycloalkyl, and the $C_{1-6}$ alkylenyl, $C_{2-6}$ alkenylenyl, $C_{2-6}$ alkynylenyl, $C_1$ O—$C_{1-6}$ alkylenyl, aryl, heteroaryl, or heterocycloalkyl can be optionally substituted with 1, 2, or 3 $C_{1-6}$ alkyl, halo, OH, aryl, or heteroaryl (preferably 1 or 2);

E can be H, aryl, heterocyclyl, heteroaryl, aryloxy, or —NHC(O)aryl wherein said aryl, heteroaryl, aryloxy, or —NHC(O)aryl is optionally substituted with 1, 2, 3, 4, or 5 halo, OH, alkoxy, CN, $C_{1-6}$ alkyl, haloalkyl, amino, alkylamino, dialkylamino, or heterocyclyl (preferably 1 or 2);

G can be H, $NR^4R^5$, or $NO_2$;

J can be H or OH;

$R^1$, $R^2$, and $R^3$ are each, independently, H, $C_{1-6}$ alkyl, or $C_{1-6}$ haloalkyl; and $R^4$ and $R^5$ are each, independently, H, $C_{1-6}$ alkyl, or $C_{1-6}$ haloalkyl.

In some embodiments, A is NH and B is $C_{1-6}$ alkylenyl optionally substituted with oxo. In some embodiments, D is absent and E is aryloxy, —NHC(O)aryl, wherein the aryl of the aryloxy or —NHC(O)aryl is optionally substituted.

In some embodiments, A is a heterocycloalkyl, e.g., a nitrogen-containing heterocyclyl such as piperidine or piperazine.

In some embodiments, G is nitro ($NO_2$).

In some embodiments, both G and J are H, and A is $NR^2C(S)NR^3$.

In some embodiments, the compound has a Formula IIa

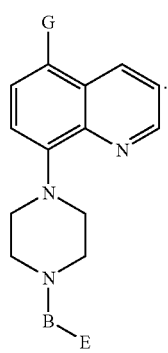

Formula IIa

In some embodiments, G is nitro ($NO_2$). In some embodiments, B is C(O) (i.e. a $C_1$ alkylenyl substituted with oxo) or $S(O)_2$. In some embodiments, E is an optionally substituted aryl or heteroaryl.

In some embodiments, the compound has a Formula IIb

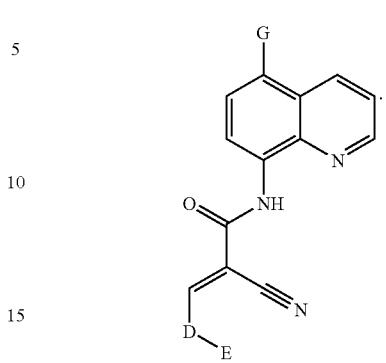

Formula IIb

In some embodiments, G is H. In some embodiments, D is heteroaryl and E is optionally substituted aryl.

Under physiological conditions (e.g. in vivo), compounds of Formula II can inhibit an activity of a sirtuin (e.g., SIRT2). In some embodiments, a compound of Formula II has an $IC_{50}$ of less than about 50 mM (e.g., less than about 25 μM, less than about 10 μM, less than about 5 μM, less than about 1 μM, or less than about 0.5 μM).

Exemplary compounds within the present invention are illustrated in FIG. 1A-FIG. 1W'. Most, but not all, of these compounds conform to Formula I or Formula II. The non-conforming compounds are also within the scope of the present invention and can be made and used as described herein.

In some embodiments, the compound is a compound of formula III

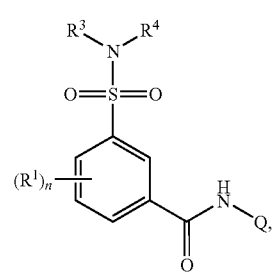

Formula III wherein each $R^1$ can independently be H, halo, $C_{1-10}$ alkyl, or $C_{1-10}$ alkoxy;

Q can be Cy or —($C_{1-6}$ alkyl)-Cy, and Cy or —($C_{1-6}$ alkyl)-Cy can be optionally substituted by 1, 2, 3, 4, or 5 substituents individually selected from halo, $C_{1-10}$ alkyl, aryl, $C_{1-10}$ haloalkyl, CN, $NO_2$, oxo, $OR^{a1}$, $C(O)OR^{a1}$, $SO_2R^3$, and $SR^1$ Cy can be cycloalkyl, 4-20 membered heterocycloalkyl, aryl, or heteroaryl (preferably 4-8);

each of $R^3$ and $R^4$ are independently $C_1$-$C_4$ alkyl, or taken together with the nitrogen to which they are attached, form a ring;

$R^{a1}$ can be H or $C_{1-10}$ alkyl;

$R^{a2}$ can be H or $C_{1-10}$ alkyl;

$R^{a3}$ can be $C_{1-10}$ alkyl;

$R^{b1}$ can be $C_{1-10}$ alkyl; and n is 0, 1, or 2.

In some embodiments, the compound is a compound of Formula IIIa is:

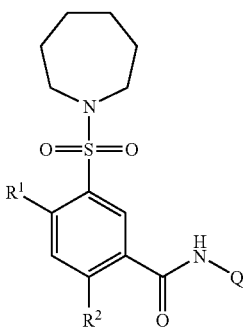

Referring to Formula IIIa, Q can be Cy or —(C$_{1-6}$ alkyl)-Cy, and Cy or —(C$_{1-6}$ alkyl)-Cy can be optionally substituted by 1, 2, 3, 4, or 5 substituents individually selected from halo, C$_{1-10}$ alkyl, aryl, C$_{1-10}$ haloalkyl, CN, NO$_2$, oxo, OR$^{a1}$, C(O)OR$^{a2}$, SO$_2$R$^{a3}$, and SR$^{b1}$;

R$^1$ can be H, halo, or C$_{1-10}$ alkyl;
R$^2$ can be H, halo, or C$_{1-10}$ alkyl;
Cy can be cycloalkyl, 4-20 membered heterocycloalkyl, aryl, or heteroaryl (preferably 4-8);
R$^{a1}$ can be H or C$_{1-10}$ alkyl;
R$^{a2}$ can be H or C$_{1-10}$ alkyl;
R$^{a3}$ can be C$_{1-10}$ alkyl; and
R$^{b1}$ can be C$_{1-10}$ alkyl.

In other embodiments, Q can be phenyl, and the phenyl moiety can be optionally substituted by 1, 2, 3, 4, or 5 substituents independently selected from halo, C$_{1-6}$ alkyl C$_{1-6}$ haloalkyl, NO$_2$, OR$^{a1}$, and C(O)OR$^{a2}$.

In other embodiments, Q can be heteroaryl, and the heteroaryl can be optionally substituted by 1, 2, 3, 4, or 5 substituents individually selected from halo, C$_{1-6}$ alkyl, aryl, C(O)OR$^{a1}$, SO$_2$R$^{a3}$, and SR$^{b1}$.

In other embodiments, Q can be heterocycloalkyl, and the heterocycloalkyl can be optionally substituted by 1, 2, 3, 4, or 5 substituents independently selected from CN, oxo, and C(O)OR$^{a2}$.

In other embodiments, Q can be —(C$_{1-6}$ alkyl)-heterocycloalkyl, and the —(C$_{1-6}$ alkyl)-heterocycloalkyl can be —(C$_{1-6}$ alkyl)-morpholino.

In other embodiments, Q can be —(C$_{1-6}$ alkyl)-heteroaryl, and the —(C$_{1-6}$ alkyl)-heteroaryl can be —(C$_{1-6}$ alkyl)-furan.

In any embodiment of Formula IIIa, R$^1$ can be H, bromo, or methyl. Alternatively, or in addition, R$^2$ can be H or chloro.

Under physiological conditions (e.g. in vivo), compounds of Formula III can inhibit an activity of a sirtuin (e.g., SIRT2). In some embodiments, a compound of Formula III has an IC$_{50}$ of less than about 50 mM (e.g., less than about 25 μM, less than about 10 μM, less than about 5 μM, less than about 1 μM, or less than about 0.5 μM).

Exemplary compounds conforming to Formula III, which are within the scope of the present invention, are illustrated in FIG. 2A-FIG. 2KK.

In some embodiments, the compound is a compound of Formula IV

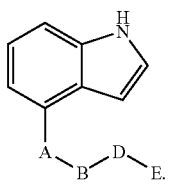

Formula IV

Referring to Formula IV, A can be absent, S, NR$^1$, NR$^2$C(S)NR$^3$, or heterocycloalkyl optionally substituted with 1, 2, 3, 4, or 5 halo, OH, CN, or C$_{1-6}$ alkyl (preferably 1 or 2);

B can be absent, C$_{1-6}$ alkylenyl, C$_{2-6}$ alkenylenyl, C$_{2-6}$ alkynylenyl, —(C$_{1-6}$ alkyl)-O—, aryl, heteroaryl, C(O), or S(O)$_2$, wherein said C$_{1-6}$ alkylenyl, C$_{2-6}$ alkenylenyl, C$_{2-6}$ alkynylenyl, —(C$_{1-6}$ alkyl)-O—, aryl, or heteroaryl is optionally substituted with 1, 2, 3, or 4 oxo, CN, OH, halo, aryl, or heteroaryl (preferably 1 or 2);

D can be absent, C$_{1-6}$ alkylenyl, C$_{2-6}$ alkenylenyl, C$_{2-6}$ alkynylenyl, O—C$_{1-6}$ alkylenyl, aryl, heteroaryl, or heterocycloalkyl, wherein said C$_{1-6}$ alkylenyl, C$_{2-6}$ alkenylenyl, C$_{2-6}$ alkynylenyl, O—C$_{1-6}$ alkylenyl, aryl, heteroaryl, or heterocycloalkyl is optionally substituted with 1, 2, or 3 C$_{1-6}$ alkyl, halo, OH, aryl, or heteroaryl (preferably 1 or 2);

E can be H, OR$^6$, aryl, heteroaryl, aryloxy, or —NHC(O)aryl, wherein said aryl, heteroaryl aryloxy, or —NHC(O)aryl is optionally substituted with 1, 2, 3, 4, or 5 halo, OH, alkoxy, CN, C$_{1-6}$ alkyl, amino, alkylamino, dialkylamino, or heterocyclyl (preferably 1 or 2);

R$^1$, R$^2$, and R$^3$ can each be, independently, H, C$_{1-6}$alkyl, or C$_{1-6}$ haloalkyl; and R$^6$ can be H or C$_{1-10}$ alkyl.

In some embodiments, A is a heterocycloalkyl, e.g., a nitrogen-containing heterocyclyl such as piperidine or piperazine.

In some embodiments, the compound is a compound of Formula IVa

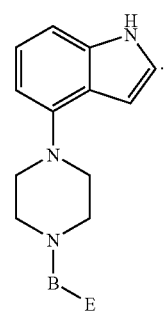

Formula IVa

In some embodiments, B is C(O) or S(O)$_2$. In some embodiments, E is an optionally substituted aryl or heteroaryl.

Under physiological conditions (e.g. in vivo), compounds of Formula IV can inhibit an activity of a sirtuin (e.g., SIRT2). In some embodiments, a compound of Formula IV has an IC$_{50}$ of less than about 50 mM (e.g., less than about 25 mM, less than about 10 mM, less than about 5 mM, less than about 1 mM, or less than about 0.5 mM).

In some embodiments, the compound is a compound of Formula V

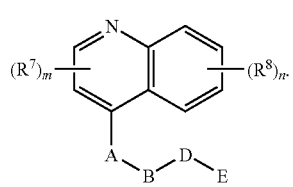

Formula V

Referring to Formula V, A can be absent, S, NR$^1$, NR$^2$C(S)NR$^3$, or heterocycloalkyl optionally substituted with 1, 2, 3, 4, or 5 halo, OH, CN, or C$_{1-6}$ alkyl (preferably 1 or 2);

B can be absent, C$_{1-6}$ alkylenyl, C$_{2-6}$ alkenylenyl, C$_{2-6}$ alkynylenyl, —(C$_{1-6}$ alkyl)-O—, aryl, heteroaryl, C(O), or S(O)$_2$, wherein said C$_{1-6}$ alkylenyl, C$_{2-6}$ alkenylenyl, C$_{2-6}$ alkynylenyl, —(C$_{1-6}$ alkyl)-O—, —(C$_{1-6}$ alkyl)-S—, aryl, or heteroaryl is optionally substituted with 1, 2, 3, or 4 oxo, CN, OH, halo, aryl, or heteroaryl preferably 1 or 2);

D can be absent, C$_{1-6}$ alkylenyl, C$_{2-6}$ alkenylenyl, C$_{2-6}$ alkynylenyl, O—C$_{1-6}$ alkylenyl, aryl, heteroaryl, or heterocycloalkyl, wherein said C$_{1-6}$ alkylenyl, C$_{2-6}$ alkenylenyl, C$_{2-6}$ alkynylenyl, O—C$_{1-6}$ alkylenyl, aryl, heteroaryl, or heterocycloalkyl is optionally substituted with 1, 2, or 3 C$_{1-6}$ alkyl, nitro, halo, haloalkyl, OH, aryl, or heteroaryl preferably 1 or 2);

E can be H, OR$^6$, aryl, heteroaryl, cycloalkyl, heterocycloalkyl, aryloxy, or —NHC(O)aryl, wherein said aryl, heteroaryl, aryloxy, or —NHC(O)aryl is optionally substituted with 1, 2, 3, 4, or 5 halo, OH, alkoxy, CN, C$_{1-6}$ alkyl, amino, alkylamino, dialkylamino, or heterocyclyl (preferably 1 or 2);

R$^1$, R$^2$, and R$^3$ can each be, independently, H, C$_{1-6}$ alkyl, or C$_{1-6}$ haloalkyl;

R$^6$ can be H or C$_{1-10}$ alkyl;

each of R$^7$ and R$^8$ can be independently alkyl, alkoxy, halo, haloalkyl, or —C(O)C$_1$-C$_6$alkyl;

m can be 0, 1, or 2 n can be 0, 1, 2, or 3

In some embodiments, A is a heterocycloalkyl, e.g., a nitrogen containing heterocyclyl such as piperidine or piperazine.

In some embodiments, m is 1 (e.g., and R$^7$ is —C(O)OC$_1$-C$_6$alkyl).

In some embodiments, n is 1 (e.g., and R$^8$ is halo).

In some embodiments, the compound is a compound of Formula Va

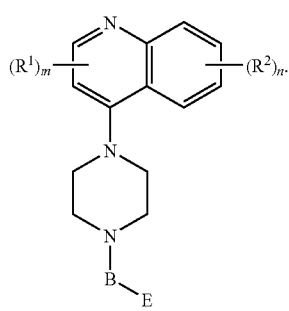

Formula Va

In some embodiments, B is C(O) or S(O)$_2$. In some embodiments, E is an optionally substituted aryl or heteroaryl.

Under physiological conditions (e.g. in vivo), compounds of Formula V can inhibit an activity of a sirtuin (e.g., SIRT2). In some embodiments, a compound of Formula V has an IC$_{50}$ of less than about 50 mM (e.g., less than about 25 μM, less than about 10 μM, less than about 5 μM, less than about 1 μM, or less than about 0.5 μM).

In some embodiments, the compound is a compound of Formula VI

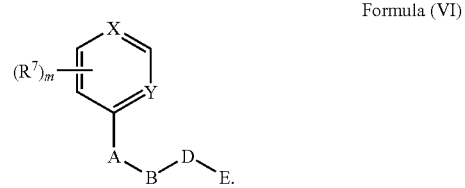

Formula (VI)

each of X and Y can be independently N, CH, or CR$^7$;

Referring to Formula VI, A can be absent, S, NR$^1$, NR$^2$C(S)NR$^3$, or heterocycloalkyl optionally substituted with 1, 2, 3, 4, or 5 halo, OH, CN, or C$_{1-6}$ alkyl (preferably 1 or 2);

B can be absent, C$_{1-6}$ alkylenyl, C$_{2-6}$ alkenylenyl, C$_{2-6}$ alkynylenyl, —(C$_{1-6}$ alkyl)-O—, aryl, heteroaryl, C(O) or S(O)$_2$, wherein said C$_{1-6}$ alkylenyl, C$_{2-6}$ alkenylenyl, C$_{2-6}$ alkynylenyl, —(C$_{1-6}$ alkyl)-O—, aryl, or heteroaryl is optionally substituted withh 1, 2, 3, or 4 oxo, CN, OH, halo, aryl, or heteroaryl preferably 1 or 2);

D can be absent, C$_{1-6}$ alkylenyl, C$_{2-6}$ alkenylenyl, C$_{2-6}$ alkynylenyl, O—C$_{1-6}$ alkylenyl, aryl, heteroaryl, or heterocycloalkyl, wherein said C$_{1-6}$ alkylenyl, C$_{2-6}$ alkenylenyl, C$_{2-6}$ alkynylenyl, O—C$_{1-16}$ alkylenyl, aryl, heteroaryl, or heterocycloalkyl is optionally substituted with 1, 2, or 3 C$_{1-6}$ alkyl, halo, OH, aryl, or heteroaryl (preferably 1 or 2);

E can be H, OR$^6$, aryl, heteroaryl, aryloxy, —NHC(O)aryl, wherein said aryl, or heteroaryl is optionally substituted with 1, 2, 3, 4, or 5 halo, OH, alkoxy, CN, C$_{1-6}$ alkyl, amino, alkylamino, dialkylamino, or heterocyclyl (preferably 1 or 2);

R$^1$, R$^2$, and R$^3$ can each be, independently, H, C$_{1-6}$ alkyl, or C$_{1-6}$ haloalkyl;

R$^6$ can be H or C$_{1-10}$ alkyl;

each R$^7$ can be independently alkyl, alkoxy, halo, nitro, haloalkyl, or —C(O)OC$_1$-C$_6$alkyl; amino, alkylamino, dialkylamino, each of which is optionally substituted with R$^8$;

each R$^8$ can be independently, cyclyl, heterocyclyl, aryl, or heteroaryl; and m is 0, 1, 2, or 3.

In some embodiments, the compound is a compound of Formula VIa

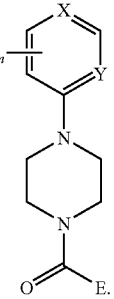

Formula (VIa)

In some embodiments, X is N and Y is CH. In some embodiments, X is CH and Y is N, In some embodiments, R$^7$ is halo. In some embodiments, E is an optionally substituted aryl or heteroaryl.

In some embodiments, the compound is a compound of Formula VIb

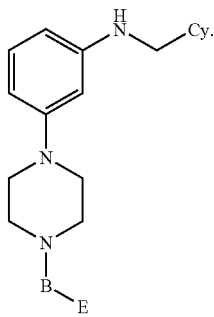

Formula VIb

In some embodiments, B is C(O) or S(O)$_2$. In some embodiments, E is an optionally substituted aryl or heteroaryl.

Under physiological conditions (e.g. in vivo), compounds of Formula VI can inhibit an activity of a sirtuin (e.g., SIRT2). In some embodiments, a compound of Formula VI has an IC$_{50}$ of less than about 50 mM (e.g., less than about 25 μM, less than about 10 μM, less than about 5 μM, less than about 1 μM, or less than about 0.5 μM).

In some embodiments, the compound is a compound of Formula VII

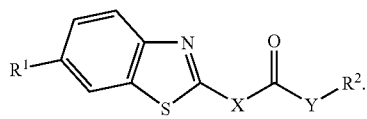

Formula VII

Referring to Formula VII, R$^1$ can be halo (e.g., fluoro), OH, alkoxy (e.g. methoxy, or ethoxy), CN, C$_{1-6}$ alkyl, amino, alkylamino, dialkylamino, or heterocyclyl;

R$^2$ can be aryl, heteroaryl, arylthio, heteroarylthio, aryloxy, or heteroarlyoxy; wherein each aryl or heteroaryl is optionally substituted with 1-3 R$^4$;

X can be NR$^3$ or alkylenyl (e.g., methylenyl);

R$^3$ can be H or C$_1$-C$_6$ alkyl;

each R$^4$ can independently be aryl, heteroaryl, alkyl, hydroxyl, alkoxy, halo, wherein each aryl or heteroaryl is optionally substituted with 1, 2, or 3 halo, OH, alkoxy, —C(O)OH, —C(O)OC$_{1-6}$ alkyl, CN, C$_{1-6}$ alkyl, amino, alkylamino, dialkylamino, or heterocyclyl; and Y can be a direct bond, —(C$_{1-6}$ alkyl)-S—, or alkylenyl.

In some embodiments, X is NH and Y is a direct bond. In some embodiments, R$^2$ is phenyl or a nitrogen containing heteroaryl.

In some embodiments, Y is methylenyl and R$^2$ is heteroarylthio. In some embodiments, the heteroaryl of the heteroarylthio is pyridinyl, or pyrimidinyl.

Under physiological conditions (e.g. in vivo), compounds of Formula VII can inhibit an activity of a sirtuin (e.g., SIRT2). In some embodiments, a compound of Formula VII has an IC$_{50}$ of less than about 50 mM (e.g., less than about 25 μM, less than about 10 μM, less than about 5 μM, less than about 1 μM, or less than about 0.5 μM).

In some embodiments, the compound is a compound of Formula VIII

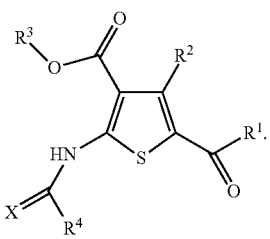

Formula VIII

Referring to Formula VIII, R$^1$ can be alkyl, hydroxyl, alkoxy, amino, alkylamino, or dialkylamino;

each of R$^2$ and R$^3$ can be H or C$_{1-6}$alkyl;

R$^4$ can be aryl, heteroaryl, arylamino, heterocycloalkylamino, or heteroarylamino, wherein aryl, heteroaryl, arylamino, heterocycloalkylamino, or heteroarylamino can be optionally substituted with 1, 2, or 3 R$^5$;

R$^5$ can be halo, OH, alkoxy, —C(O)OH, —C(O)OC$_{1-6}$ alkyl, CN, C$_{1-6}$ alkyl, —SO$_2$NH$_2$, amino, alkylamino, dialkylamino, or heterocyclyt; and X can be O or S.

In some embodiments, R$^2$ is C$_{1-6}$alkyl (e.g., methyl). In some embodiments, R$^3$ is C$_{1-6}$alkyl (e.g., ethyl or isopropyl).

In some embodiments, X is O and R$^4$ is aryl (e.g., phenyl).

In some embodiments, X is S and R$^4$ is heteroarylamino.

Under physiological conditions (e.g. in vivo), compounds of Formula VIII can inhibit an activity of a sirtuin (e.g., SIRT2). In some embodiments, a compound of Formula VIII has an IC$_{50}$ of less than about 50 mM (e.g., less than about 25 μM, less than about 10 μM, less than about 5 μM, less than about 1 μM, or less than about 0.5 μM).

In some embodiments, the compound is a compound of Formula IX

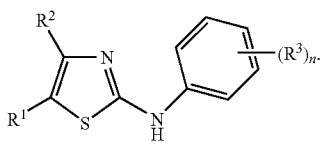

Formula IX

Referring to Formula IX, R$^1$ can be H, or C(O)R$^4$;

R$^2$ can be H, amino, heterocycloalkyl, aryl, or heteroaryl; wherein aryl or heteroaryl can be optionally substituted with halo, OH, alkoxy, —C(O)OH, —C(O)OC$_{1-6}$ alkyl, CN, C$_{1-6}$ alkyl, amino, alkylamino, dialkylamino, or heterocyclyl;

R$^3$ can be halo, OH, alkoxy, —C(O)OH, —C(O)OC$_{1-6}$ alkyl, CN, C$_{1-6}$ alkyl, amino, alkylamino, dialkylamino, or heterocyclyl;

R$^4$ is aryl or heteroaryl, optionally substituted with 1, 2, or 3 R$^5$;

R$^5$ can be halo, OH, alkoxy, —C(O)OH, —C(O)OC$_{1-6}$ alkyl, CN, C$_{1-6}$ alkyl, amino, alkylamino, dialkylamino, or heterocyclyl;

n can be 0, 1, 2, or 3.

In some embodiments, R$^1$ is H. In some embodiments, R$^1$ is C(O)aryl, wherein aryl is optionally substituted.

In some embodiments, R$^2$ is amino. In some embodiments, R$^2$ is heteroaryl, e.g., a bicyclic heteroaryl, optionally substituted, for example, with methyl.

In some embodiments, R$^3$ is halo or methoxy and n is 1.

Under physiological conditions (e.g. in vivo), compounds of Formula IX can inhibit an activity of a sirtuin (e.g., SIRT2). In some embodiments, a compound of Formula IX has an $IC_{50}$ of less than about 50 mM (e.g., less than about 25 μM, less than about 10 μM, less than about 5 μM, less than about 1 μM, or less than about 0.5 μM).

In some embodiments, the compound is a compound of Formula X

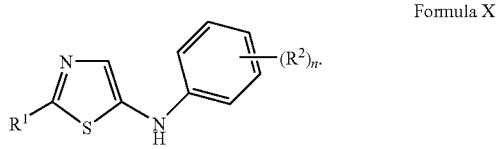

Formula X

Referring to Formula X, $R^1$ can be heterocycloalkyl, aryl, or heteroaryl, optionally substituted with 1, 2, or 3 $R^3$;

$R^2$ can be halo, OH, alkoxy, —C(O)OH, —C(O)O$C_{1-6}$ alkyl, CN, $C_{1-6}$ alkyl, amino, alkylamino, dialkylamino, or heterocyclyl;

$R^3$ can be halo, OH, alkoxy, —C(O)OH, —C(O)O$C_{1-6}$ alkyl, CN, $C_{1-6}$ alkyl, amino, alkylamino, dialkylamino, or heterocyclyl;

n can be, 1, 2, or 3.

In some embodiments, $R^1$ is heteroaryl, e.g., a nitrogen containing, fused heteroaryl, optionally substituted. In some embodiments, $R^1$ is substituted with 1 or 2 alkyl (e.g., methyl).

In some embodiments, $R^2$ is alkoxy (e.g., methoxy) or dialkylamino and n is 1.

Under physiological conditions (e.g. in vivo), compounds of Formula X can inhibit an activity of a sirtuin (e.g., SIRT2). In some embodiments, a compound of Formula X has an $IC_{50}$ of less than about 50 mM (e.g., less than about 25 μM, less than about 10 μM, less than about 5 μM, less than about 1 μM, or less than about 0.5 μM).

The compounds described herein (e.g., compounds of formulae I-X) can be used in methods of treating a subject, including a human patient (e.g., a human patient who has been diagnosed as having a disorder associated with expression of a sirtuin). More specifically, the methods can be carried out by identifying a subject who has been diagnosed as having, or who is at risk of developing, a disorder that is associated with, or mediated at least in part by, a sirtuin and administering to the subject a therapeutically effective amount of a pharmaceutical composition described herein (e.g., a pharmaceutical composition that includes a compound as described herein). The subject can be a subject (or "patient") diagnosed as having, or one who is at risk of developing, a disorder characterized by unwanted cellular proliferation; a neurological disorder; a disorder prevalent in the elderly; or a metabolic disorder. More specifically, disorders characterized by unwanted cellular proliferation can be neoplastic disorders and include cancer (e.g., breast cancer, neuroblastoma, or myeloma) and non-malignant growths. Disorders classified as neurological disorders include Huntington's disease (an aggregation associated disease), Parkinson's disease, Alzheimer's disease, spinal and bulbar muscular atrophy, dentatorubral-pallidoluysian atrophy, spinocerebellar ataxia type 1 (SCA1), SCA2, SCA6, SCA7, Machado-Joseph disease (MJD/SCA3), and Creutzfeldt-Jakob disease. Disorders prevalent in the elderly include dementia, osteoporosis, hypertension, unsteady gait and difficulty maintaining balance. The present compounds can also benefit and can be administered to adult and elderly patients generally, whether or not they have a disorder associated with aging. The metabolic disorders include amyloidosis, alpha-1-antitrypsin deficiency disease, diabetes (e.g., type I or type II diabetes), metabolic syndrome, and atherogenic dyslipidemia. A present compound can also be used to treat subjects who are overweight or obese.

The invention also encompasses pharmaceutically acceptable salts or solvates of a compound described herein (e.g., a compound of formulae I-X) and prodrugs, metabolites, structural analogs, and other pharmaceutically useful variants thereof. These other variants may be, for example, complexes containing the compound and a targeting moiety, as described further below, or a detectable marker (e.g., the compound may be joined to a fluorescent compound or may incorporate a radioactive isotope). When in the form of a prodrug, a compound is modified in vivo (e.g., intacellularly) after being administered to a patient or to a cell in culture. The modified compound (i.e., the processed prodrug) will be identical to a compound described herein and will be biologically active or have enough activity to be clinically beneficial. Metabolites are the products resulting from intracellular modification of the present compounds.

Packaged products (e.g., sterile containers containing one or more of the compounds described herein and packaged for storage, shipment, or sale) and kits, including at least one compound of the invention and instructions for use, are also within the scope of the invention.

In one aspect, the invention features substantially pure preparations of the compounds described herein or combinations thereof. A naturally occurring compound is substantially pure when it is separated to some degree from the compound(s) or other entities (e.g., proteins, fats, or minerals) it is associated with in nature. For example, a naturally occurring compound described herein is substantially pure when it has been separated from at least (or about) 50%, 60%, 70%, 75%, 80%, 85%, 90%, 95%, 96%, 97%, 98%, 99% or more of the compound(s) or other moieties it is associated with in nature (presuming it is a naturally occurring compound). While the compounds of the invention may be naturally occurring and may be purified using conventional techniques, they may also be non-naturally occurring and may be synthesized (naturally occurring compounds can be synthesized as well). Compounds prepared by chemical synthesis are substantially pure, as are compounds that have been separated from a library of chemical compounds (e.g., separated from at least (or about) 50%, 60%, 70%, 75%, 80%, 85%, 90%, 95%, 96%, 97%, 98%, 99% or more of a library of which they are a part). A substantially pure compound may be one that is separated from all the other members of the compound library or it may be one that has been separated to a limited extent (e.g., it may remain associated with a limited number (e.g., 1, 2, 3, 4, or 5-10) of other members of the library). A compound library or a substantial portion thereof is not a pharmaceutical or therapeutic composition.

Regardless of their original source or the manner in which they are obtained, the compounds of the invention can be formulated in accordance with their use. For example, the compounds can be formulated within compositions for application to cells in tissue culture or for administration to a patient. For example, the compounds can be mixed with a sterile pharmaceutically acceptable diluent (such as normal saline). As noted below, and as known in the art, the type of diluent can vary depending upon the intended route of administration. The resulting compositions can include additional agents, such as preservatives. The compounds may also be applied to a surface of a device (e.g., a catheter), administered orally or parenterally, or contained within a pump, patch, or other drug delivery device.

We may refer to a substance (e.g., a protein, such as an intracellular protein) that is affected by a compound as a target (e.g., a target protein). The target may be the protein or other agent most directly involved with, or associated with, a disorder or disease process (e.g., the target can be a sirtuin (e.g., SIRT2) per se). Alternatively, the target can be a protein or the like (e.g., a glycoprotein, protein complex, or peptide) that is active upstream or downstream in a biochemical pathway in which the primary target (e.g., SIRT2) is active. We may refer to these targets as secondary targets. For example, the secondary target protein can be a transcription factor that facilitates expression of a gene encoding a primary target protein. The secondary target protein could also be a protein whose activity changes upon interacting with the primary target protein. For example, where the primary target protein is an enzyme, the secondary target protein can be that enzyme's substrate or a cofactor (e.g., a compound may specifically inhibit the interaction between a sirtuin (e.g., SIRT2) and its substrate or a cofactor that participates in the enzymatic reaction). The compounds of the invention may also (or may alternatively) affect protein or RNA stability, thereby affecting sirtuin activity or polypeptide accumulation within a cell, and may also modulate the post-translational processing of a protein. For example, a compound may interact with a kinase, phosphatase, methyl transferase, ubiquitinase, protease, polymerase, or other enzyme that modifies a sirtuin or another component upstream or downstream in a sirtuin pathway. A co-factor (e.g., NAD) can also be a secondary target. These scenarios are meant to describe the manner in which the compounds of the invention may exert their effect on a cell and, more generally, on a patient, but the invention is not so limited. The invention encompasses compounds according to the formulas described herein, the variants described herein (e.g., salts), compositions containing them (e.g., pharmaceutical formulations), and methods of using them regardless of the mechanism by which they work. Primary and secondary targets could be polyQ-containing or glutamine-rich polypeptides.

In addition to determining the effect of a compound on sirtuin activity, one can carry out assays or screens including a step (or steps) in which one determines cellular toxicity. Compounds that modulate (e.g., inhibit or enhance) sirtuin activity and are non-toxic, can be further assessed in animal models of a sirtuin-associated disorder and may then progress to clinical trials. One can also generate a dose response profile of putative assay hits and record the results in a screening database. As noted, compounds as described herein that alter sirtuin activity are withing the present invention as are screening or assay methods having the steps described above and the screening database.

In specific embodiments, the compositions of the present invention can be administered to a subject who has, who has been diagnosed with, or who is at risk of developing: immunoglobulin light chain amyloidosis, HD, Parkinson's disease, adult-onset diabetes, cirrhosis (e.g., cirrhosis of the liver), emphysema, or a prion disease, such as Creutzfeldt-Jakob disease. Other conditions that can be treated or prevented with one or more of the present compounds include amyotrophic lateral sclerosis, dentatorubral pallidoluysian atrophy, spinal bulbar muscular atrophy (SBMA; also known as Kennedy's disease), any of the several types of spinocerebellar ataxias (e.g., SCA1, SCA2, SCA6, SCA7 and Machado-Joseph disease (MJD/SCA3)), dentatorubral-pallidoluysian atrophy, disorders in which polyglutamine-containing transcription factors or coactivators are undesirably active (e.g., disorders associated with homodimerization of jun or hexamerization of p53), and disorders in which one or more of the sirtuins are undesirably overactive. For example, a subject may have been diagnosed as having, or at risk for developing, a carcinoma (e.g., breast cancer), amyloidosis, a myeloma, kuru, a neuroblastoma, cystic fibrosis, or an alpha-1-antitrypsin deficiency disease.

Therapeutic methods featured in the invention can include the step of identifying a subject in need of treatment. The subject can be identified by, for example, a health care professional (e.g., a physician) on the basis of subjective or objective information (e.g., based on comments from the subject, a physical examination, and/or on measurable parameters (i.e., diagnostic tests)). Subjects who are treated with the compounds featured in the invention may have been diagnosed with any disease associated with sirtuin activity. Alternatively, the subject may be at risk for developing these disorders. For example, a subject may have a family history or a genetic mutation or element that contributes to the development of a sirtuin-associated disorder. Human subjects, in consult with their physicians and/or other health care professionals, can decide whether their risk is great enough to undergo preventative care, as is the case for any prophylactic treatment or procedure. While the subjects of the preventative and/or therapeutic regimes described herein may be human, the compounds and compositions of the invention can also be administered to non-human subjects (e.g., domesticated animals (such as a dog or cat), livestock (e.g., a cow, pig, sheep, goat, or horse), or animals kept in captivity (e.g., any of the large cats, non-human primates, zebra, giraffes, elephants, and the like kept in zoos, parks, or preserves)).

The prophylactic and therapeutic methods can be carried out by administering to the subject a pharmaceutical composition containing a therapeutically effective amount of one or more of the compounds described herein. While a single compound may be effective, the invention is not so limited. A subject can be treated with multiple compounds, administered simultaneously or sequentially (i.e., before or after a compound of the present invention). For example, a subject can be treated with one or more of the compounds described herein and, optionally, a chemotherapeutic agent, an analgesic, a bronchodilator, levodopa or a similar medication, haloperidol, or risperdone. In other embodiments, the "second" agent can be a vitamin, mineral, nucleic acid (e.g., an antisense oligonucleotide or siRNA), a therapeutic protein (e.g., a peptide), including therapeutic antibodies or antigen-binding portions thereof, or an anti-inflammatory agent. Compositions containing a compound of the invention and a second agent, as described herein, are also within the scope of the present invention.

The combination therapy will, of course, depend on the disorder being treated. Where a compound of the invention is administered to treat a patient with a cancer, it may be combined with a known chemotherapeutic agent used to treat that type of cancer (e.g., a chemotherapeutic agent, a radioisotope, or a cytotoxin). Examples of chemotherapeutic agents include taxol, cytochalasin B, gramicidin D, mitomycin, etoposide, tenoposide, vincristine, vinblastine, colchicin, busulfan, cisplatin, doxorubicin, daunorubicin, dihydroxy anthracin dione, mitoxantrone, mithramycin, chlorambucil, gemcitabine, actinomycin, procaine, tetracaine, lidocaine, propranolol, puromycin, maytansinoids and analogs or homologs thereof. Additional therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carnustine (BSNU) and lomustine (CCNU), cyclothosphamide, husulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mitfiramycin, and anthramycin (AMC)), and anti-mitotic agents (e.g., vincristine, vinblastine, taxol and maytansinoids). Radioisotopes can include alpha, beta and/or gamma emitters. Examples of radioisotopes include $^{212}$Bi, $^{213}$Bi, $^{131}$I, $^{211}$At, $^{186}$Re, $^{90}$Y and $^{117}$Lu. Where a compound of the invention is administered to treat a patient with Parkinson's disease, it may be combined with a medication to increase dopamine levels in the brain; and so forth.

With respect to "sirtuin-associated" disorders, the predominant theory is that sirtuins' enzymatic activities or overactivities are deleterious, in which case a sirtuin inhibitor would be beneficial. However, a contrary theory holds that, at least some disorders are causally associated with underactive sirtuins. In that event, the compound of choice would be one that enhances or promotes sirtuin activity. This scenario is reminiscent of that regarding protein aggregation in diseases such as Huntington's disease. While a dominant theory holds that protein-protein aggregation is deleterious, there is reason to believe that promoting aggregation is a cellular defense mechanism; harmful proteins aggregate, forming large inclusions that are targeted by, and slowly degraded by, cellular enzymes. If the latter theory proves true to any extent, compounds that facilitate aggregation will be efficacious therapeutic agents. In our studies, some of which are presented below in the "Examples", we have observed the formation of large inclusions upon the treatment of cells with some of the compounds described herein.

The present compounds can be formulated for use in cell culture and/or for in vivo administration (in treating or preventing a sirtuin-associated disorder) and supplied as reagents for research, as described herein. For example, the compounds can be used to generate cellular or animal models of the diseases described above, and the cellular or animal models can include a step of determining a dose response profile and cellular toxicity.

Where ranges are provided (e.g., numerical ranges), unless the context clearly indicates otherwise, it is to be understood that the invention encompasses the endpoint values as well as all those inbetween. For example, where a portion of a compound is $C_{1-6}$ alkylenyl, the alkylenyl may have 1, 2, 3, 4, 5, or 6 carbon atoms. The same is true where a given range accommodates more than whole integers (i.e., where a range may include fractions of whole units (e.g., dosage units)).

Other features and advantages of the invention will be apparent from the accompanying drawings and description, and from the claims.

BRIEF DESCRIPTION OF THE DRAWINGS

FIGS. 5A-5G are representations of eight tested compounds (FIG. 5A) and the results achieved with these compounds in assays of SIRT2 and SIRT3 activity (FIGS. 5B and 5C, respectively, with each compound tested at a single dose concentration of 10 μM). The table (FIG. 5D) depicts $IC_{50}$ values for the eight compounds against various sirtuins. As shown in the table and in the inhibition profile for AGKZ (compound "2" of FIG. 5A), SIRT2 is inhibited by AGK2 with a calculated $IC_{50}$ value of 3.5 μM (FIG. 5E). This represents a10-fold increase in potency of AGK2 over B2. To determine the relative selectivity of AGK2 for SIRT2, we tested this compound against SIRTT and SIRT3. AGK2 slightly inhibits SIRT1 and SIRT3 at compound concentrations of 40 μM or higher, demonstrating that AGK2 is indeed selective for SIRT2 (FIGS. 5F and 5G, respectively).

FIG. 8 is a representation of the amino acid sequences of human SIRT1, SIRT2, and SIRT3, which can be used in the assays described herein.

DETAILED DESCRIPTION

Figure 1H:
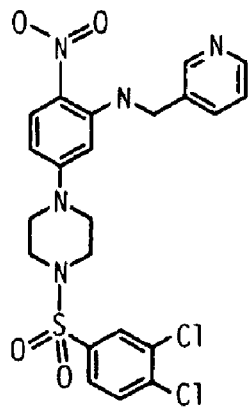
FIG. 1A-1W' are exemplary compounds.
Figure 1I:
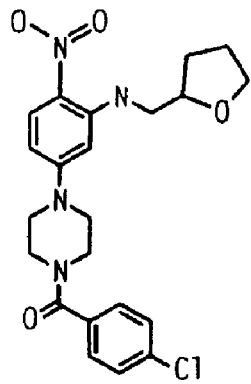
Figure 1J:
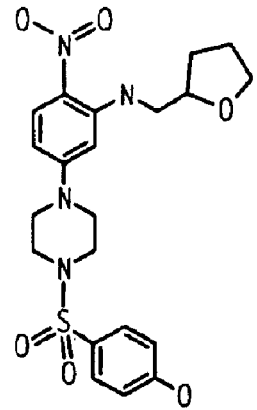
Figure 1K:
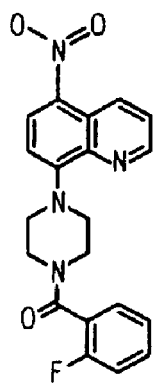
Figure 1L:
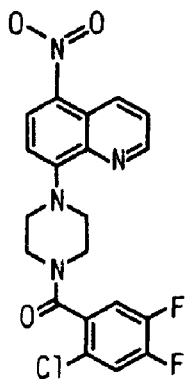
Figure 1M:
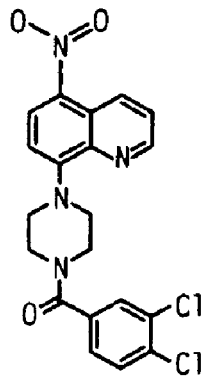
Figure 1N:
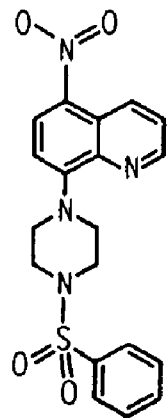
Figure 1O:
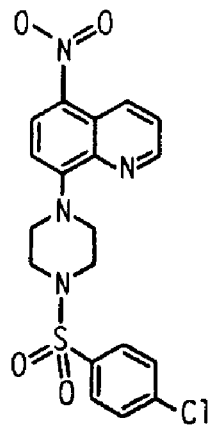
Figure 1P:
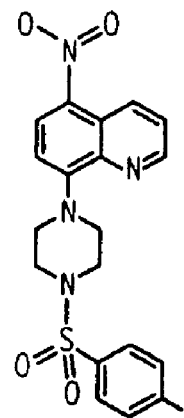
Figure 1Q:
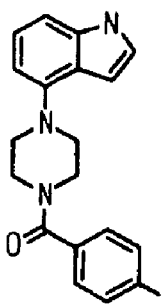
Figure 1R:
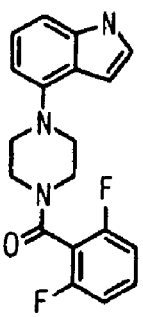
Figure 1S:
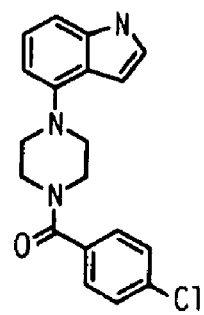
Figure 1T:
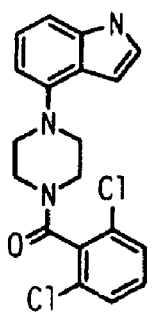
Figure 1U:
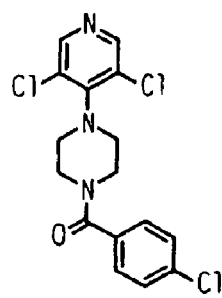
Figure 1V:
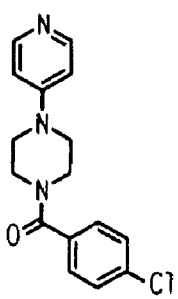
Figure 1W:
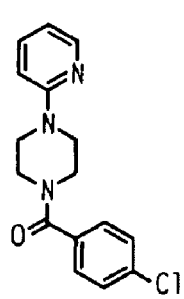
Figure 1X:
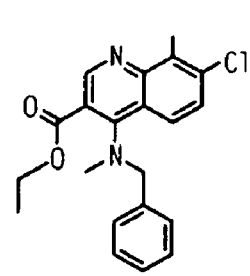
Figure 1Y:
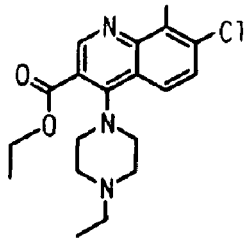
Figure 1Z:
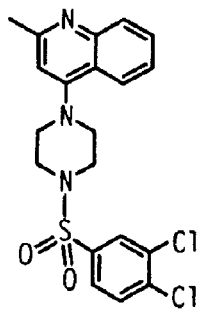
Figure 1A:
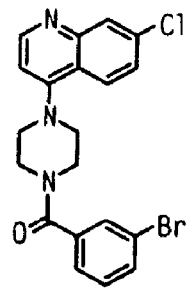
Figure 1B:
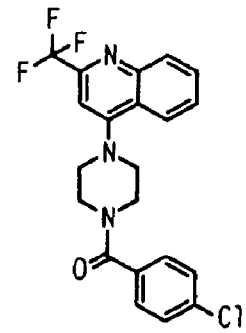
Figure 1C:
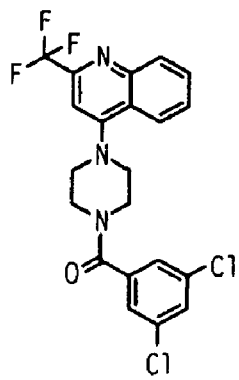
Figure 1D:
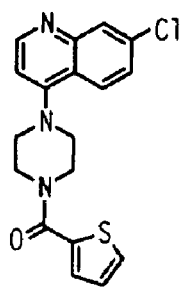
Figure 1E:
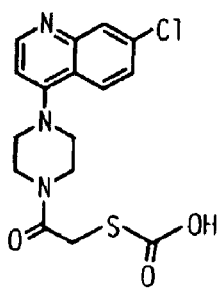
Figure 1F:
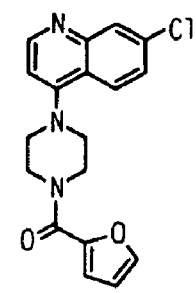
Figure 1G:
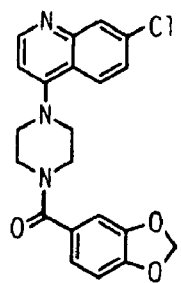
Figure 1H:
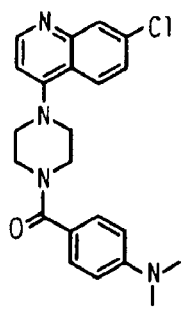
Figure 1I:
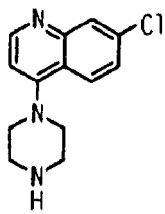
Figure 1J:
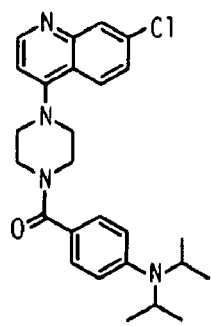
Figure 1K:
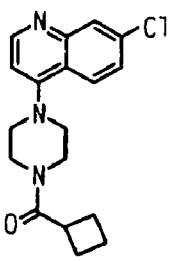
Figure 1L:
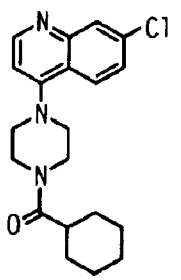
Figure 1M:
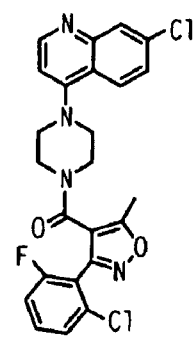
Figure 1N:
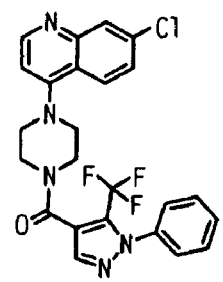
Figure 1O:
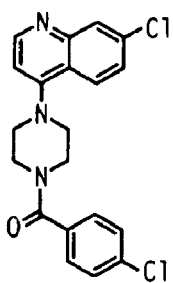
Figure 1P:
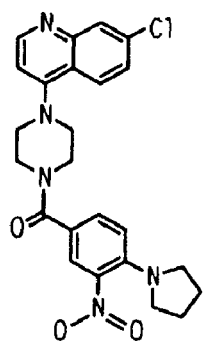
Figure 1Q:
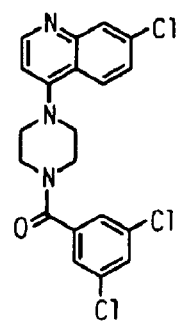
Figure 1R:
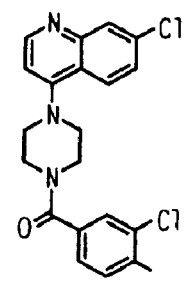
Figure 1S:
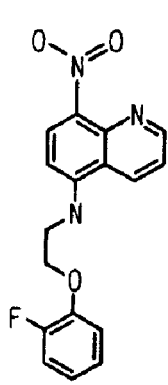
Figure 1T:
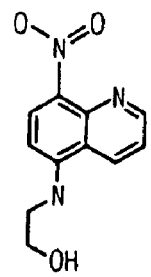
Figure 1U:
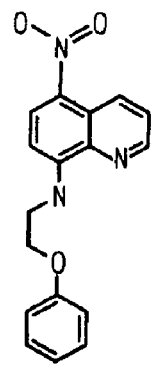
Figure 1V:
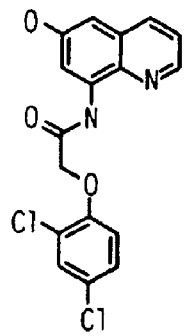
Figure 1W:
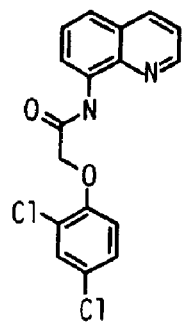
Figure 1X:
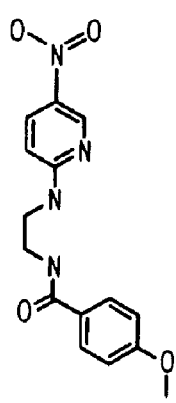
Figure 1Y:
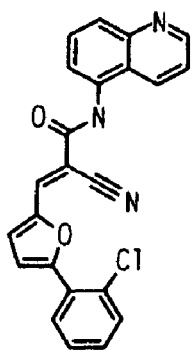
Figure 1Z:
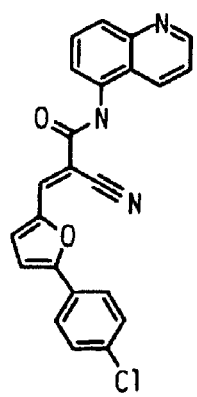
Figure 1A:
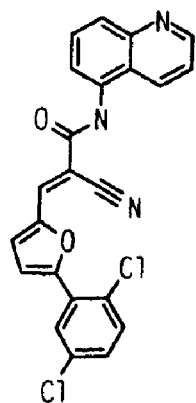
Figure 1B:
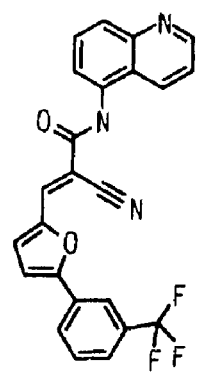
Figure 1C:
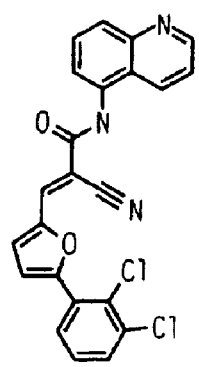
Figure 1D:
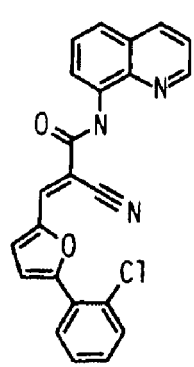
Figure 1E:
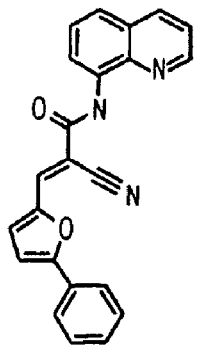
Figure 1F:
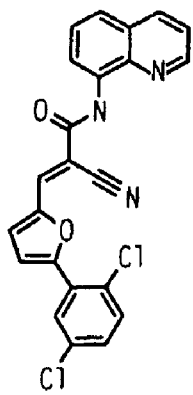
Figure 1G:
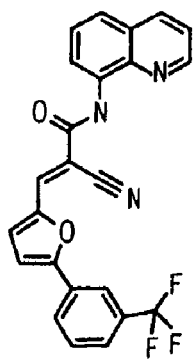
Figure 1H:
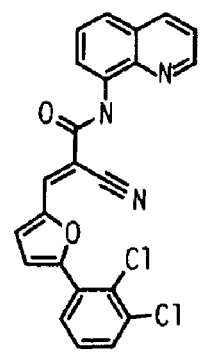
Figure 1Q:
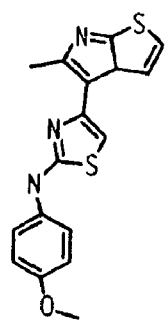
Figure 1R:
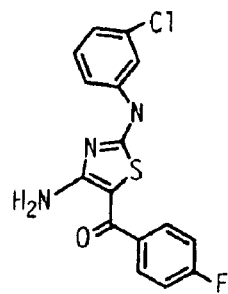
Figure 1S:
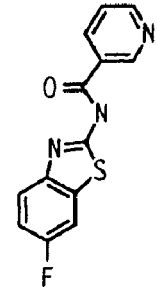
Figure 1T:
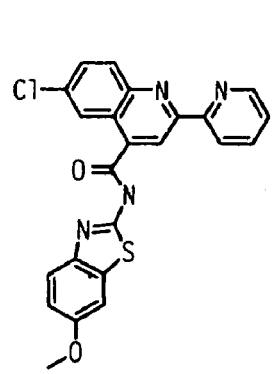
Figure 1U:
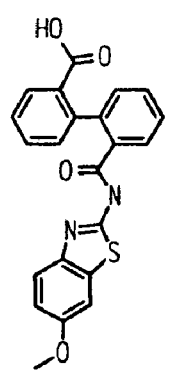
Figure 1V:
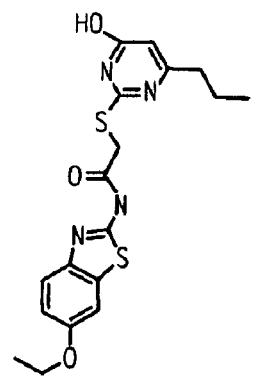
Figure 1W:
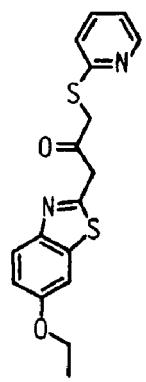
Figure 2A:
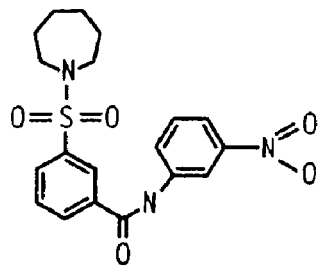
FIG. 2A-2MM are exemplary compounds.
Figure 2B:
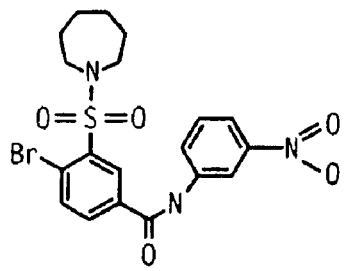
Figure 2C:
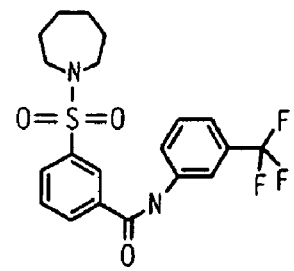
Figure 2D:
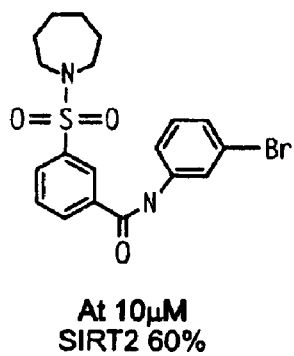
Figure 2E:
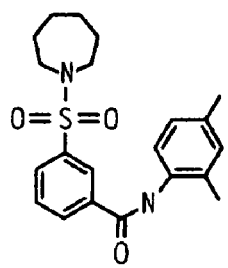
Figure 2F:
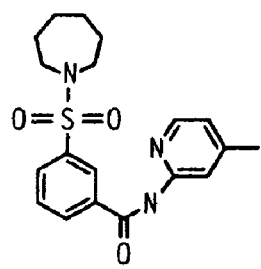
Figure 2G:
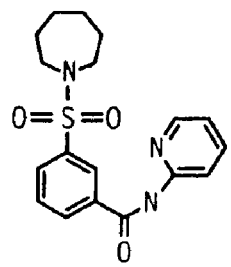
Figure 2H:
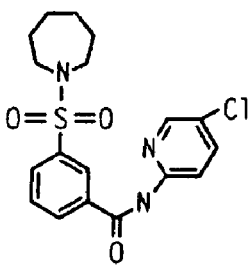
Figure 2I:
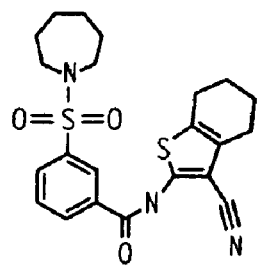
Figure 2V:
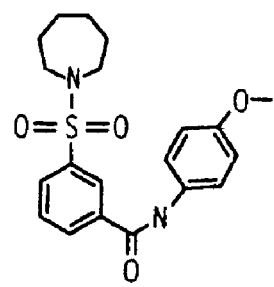
Figure 2W:
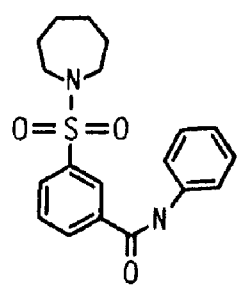
Figure 2X:
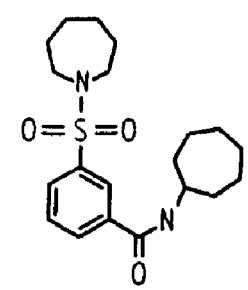
Figure 2Y:
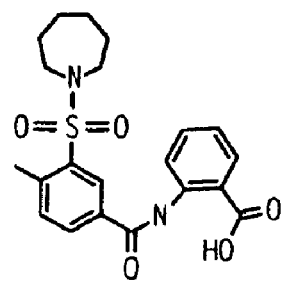
Figure 2Z:
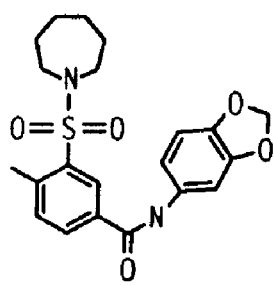
Figure 2A:
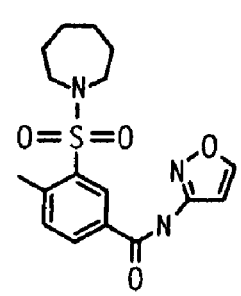
Figure 2B:
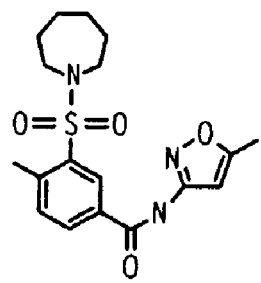
Figure 2C:
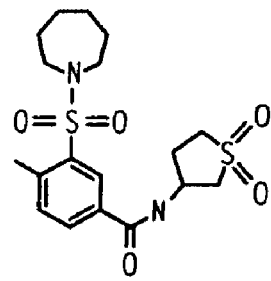
Figure 2D:
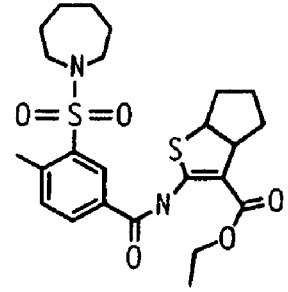
Figure 2E:
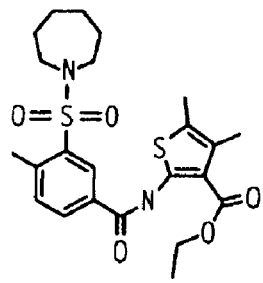
Figure 2F:
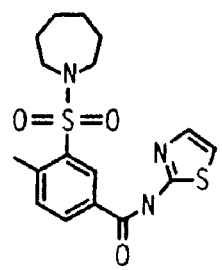
Figure 2G:
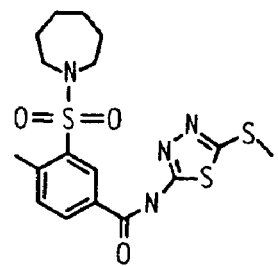
Figure 2H:
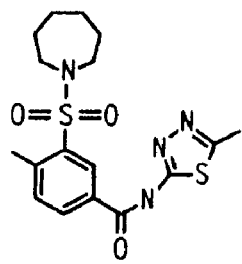
Figure 2I:
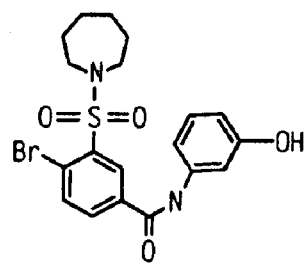
Figure 2J:
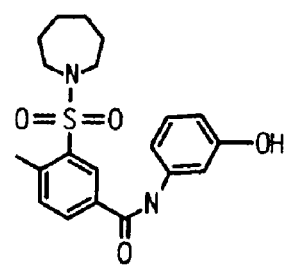
Figure 2K:
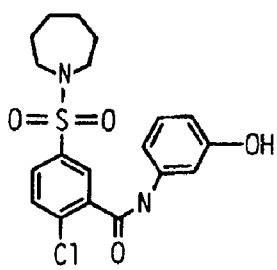
Figure 2L:
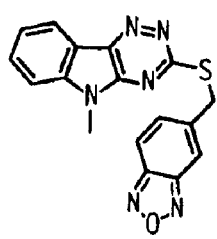
Figure 2M:
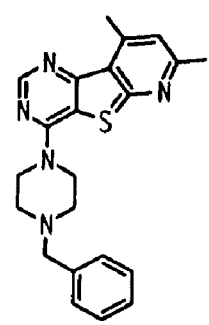

The present invention is based, in part, on our discovery of compounds that inhibit an activity of a sirtuin (e.g., compounds that inhibit or preferentially inhibit an activity of SIRT2) and are therefore believed useful in the treatment or prevention of diseases associated with sirtuin activity. For example, a compound that inhibits SIRT2 to a greater extent that it inhibits another sirtuin preferentially inhibits SIRT2. Compounds that inhibit one sirtuin but do not inhibit any other sirtuin to any appreciable extent may be described as strongly preferential. For example, a compound that inhibits SERT2 but does not inhibit any other human sirtuin is a strongly preferential inhibitor of SIRT2. Accordingly, the present compounds are ones that affect a cell in a desirable way and we expect, mechanistically, that the desired effect will be achieved by the compound's ability to inhibit an activity in which a sirtuin (e.g., SIRT2) is normally engaged to an experimentally or clinically useful extent. For example, the compound may affect (e.g., inhibit) deacetylase activity by acting on the sirtuin, its substrate, a cofactor (e.g., NAD or an NAD analog), or binding partner.

The present compounds can be administered alone or in combination with each other or other (e.g., known) therapeutic agents. Where one or more compounds are used in combination with another therapeutic agent, the compound(s) will provide a superior experimental paradigm or an improved clinical outcome relative to that expected with the therapeutic agent alone. Formulations and methods of administering the present compounds are described further below.

Activity (e.g., deacetylase activity) can be assessed with respect to a natural sirtuin substrate (e.g., a natural SIRT2 substrate) in vitro, in a cell, tissue, or organ culture, or in vivo. A compound's activity as a sirtuin inhibitor can also be assessed with respect to an artificial substrate and/or with respect to the sirtuin's ability to interact with a cofactor or binding partner that is necessary for enzymatic activity. For example, any given compound can be assessed for an ability to inhibit an activity (e.g., deacetylase activity) of a sirtuin (e.g., SIRT2 (e.g., human SIRT2)) by presenting a substrate to the sirtuin in the presence of the compound and under conditions (e.g., physiological conditions) suitable for an enzymatic reaction to occur. A "control", such as an assay carried out under comparable conditions but in the absence of the compound, can also be performed. As noted, the substrate presented for deacetylation can be a naturally occurring protein and/or a natural substrate of the sirtuin being assessed or a non-naturally occurring (e.g., truncated) and/or a non-natural substrate of the sirtuin being assessed.

Natural substrates of SIRT1 include histones, p53, and FoxO transcription factors such as FoxO1 and FoxO3. Any protein or protein-containing compound to which a sirtuin binds or with which it interacts to deacetylate a substrate may be referred to as a "binding partner." For example, SIRT1 binds to p53 and plays a role in the p53 pathway. More specifically, SIRT1 can deacetylate certain lysines of p53 (e.g., K370, K371, K372, K381, and/or K382 of p53) and one can readily determine whether a compound interferes with, or promotes, SIRT1's ability to deacetylate p53. As noted above, artificial substrates can also be used to assess the extent to which a compound affects the activity of a sirtuin, and exemplary artificial substrates include protein substitutes of p53 (e.g., fragments of p53 that include one or more of the lysine residues corresponding to those found at positions 370-382 of p53).

As noted, SIRT1 proteins can also deacetylate histones. For example, SIRT1 can deacetylate lysines 9 and/or 14 of histone H3 or peptides, including small peptides, that include one or both of these lysines. Histone deacetylation alters local chromatin structure and consequently contributes to gene transcription in the vicinity of the altered chromatin. Many of the SIRT1 binding partners are transcription factors that recognize specific DNA sequences. For example, SirT1 deacetylates and downregulates forkhead proteins (i.e., FoxO proteins). Because of the interaction between sirtuins (e.g., SIRT1 or SIRT2) and their binding partners (e.g., a SIRT1 or SIRT2 binding partner, respectively) sirtuins can be used to deliver binding partners, which may be tagged or otherwise modified in ways that affect a cell (e.g., modified by linkage to a toxin), to specific regions of the cell (e.g., the nucleus and DNA therein). The compounds of the invention may affect a sirtuin's ability to deacetylate a substrate interfering with the sirtuin's interaction with a binding partner.

Human SIRT2 is an ortholog of the *S. cerevisiae* protein Sir2p (silent information regulator 2 protein). SIRT2 is located predominantly in the cytoplasm and colocalizes with microtubules (see North et al., *Mol. Cell.* 11:437-444, 2003). SIRT2 deacetylates lysine-40 of alpha-tubulin both in vitro and in vivo, and knockdown of SIRT2 with siRNA results in tubulin hyperacetylation (North et al., supra). SIRT2 colocalizes and interacts in vivo with HDAC6, another tubulin deacetylase. Enzymatic analysis of recombinant SIRT2 in comparison to a yeast homolog of Sir2 protein (Hst2p) indicates that SIRT2 has a preference for acetylated tubulin peptide as a substrate relative to acetylated histone H3 peptide North et al., supra). Accordingly, acetylated tubulin (e.g., an alpha-tubulin) and histone H3 peptides can serve as substrates in assays of the present compounds. Variants of the naturally occurring substrates can also be used, and SIRT2 activity can be assessed in vitro, in a cell, tissue, or organ culture, or in vivo. Exemplary substrates for SIRT2 include peptides that are portions of alpha-tubulin having the lysine residue at position 40 of alpha-tubulin.

Other exemplary sirtuin substrates include cytochrome c and acetylated peptides thereof.

We often refer to "a sirtuin" or to "sirtuins" generally, and we tend to refer to particular sirtuins by name (e.g., simply as "SIRT1," "SIRT2," and so forth). As sirtuins are proteins, we may also use terms such as "SRT2 protein" or "SIRT2 polypeptide" interchangeably. The present compounds can be assessed with respect to their effect on a full-length sirtuin (e.g., SIRT1 or SIRT2), or an assay can be configured to use a variant thereof. For example, one can use a fragment of a sirtuin that is capable of deacetylating a substrate in the presence of NAD and/or an NAD analog and/or a fragment of a sirtuin that is capable of binding a target protein or binding partner (e.g., a transcription factor or a tubuli (e.g., alpha-tubulin). For example, the variant sirtuin can include a conserved catalytic domain. Where we refer to a "full-length" sirtuin (e.g., SIRT1 or SIRT2), we are referring to a polypeptide that has at least the sequence of a naturally-occurring sirtuin. The sequences of human SIRT1, SIRT2, and SIRT3 are shown in FIG. 8.

A full-length sirtuin or a fragment or other variant thereof can also include other sequences (e.g., a purification tag, marker, label (e.g., an attached fluorophore or other detectable marker), or cofactor).

A sirtuin "activity" refers to a biological activity normally carried out by a sirtuin. The activity can be deacetylation of a substrate (e.g., an amino acid residue within a peptide or a protein; as described herein and known in the art, enzymes exhibit certain specificities, and certain sirtuins deacetylate certain substrates). The activity can also be a non-deacetylating interaction with another protein. For example, the activity can be an interaction with a transcription factor such as p53, a tubulin such as alpha-tubulin, or a histone protein. The interaction can include, or can occur in the presence of, a cofactor such as NAD and/or an NAD analog, and may be described as binding with a target protein or binding partner.

Small molecule-based therapeutics have provided the means to successfully treat many diseases, and the identification of pharmacological agents that can reverse, block, or delay disease-linked processes in model systems is critical to the development of effective treatments for the diseases described herein. Our assays employ model systems that recapitulate key features of disease pathology and that are adaptable to high throughput screening against a large collection of chemical compounds.

Using our assays and screens, we have identified compounds we believe are capable of modulating (either directly or indirectly) the activity of SIRT2 and/or an association of polypeptides including those that, when abnormally expressed or associated, cause pathological disorders such as Parkinson's disease, Huntington's disease, and the other disorders referred to herein (we tend to use the term "disorder" to refer to any disease, unwanted condition, or syndrome). The compounds described herein can be used to modulate (e.g., inhibit) SIRT2 and/or the aggregation of polypeptides, such as polyQ-containing polypeptides that are associated with pathological disorders, as well as non-naturally occurring polypeptides (e.g., polyQ-containing polypeptides that are used in disease models, such as models of HD). Any assay in which one can assess the enzymatic activity of a sirtuin (e.g., SIRT2) can be used. The assay can be an in vitro assay, an assay carried out in cell or tissue culture, or an assay conducted in an animal model. More specifically, in vitro and cell-based assays can be fluorimetric activity assays. Activity can be assessed with respect to any sirtuin (e.g., SIRT2) by assessing the sirtuin's ability to deacetylate a substrate. The substrate can be any naturally occurring substrate or a synthetic peptide substrate (for SIRT1, such a peptide has been described by Howitz et al., *Nature* 425:191-196, 2003). By way of example, SIRT2 activity has been tested using acetylated HeLa histones (Grozinger et al., *J. Biol. Chem.* 276:38837-38843, 2001). 1.5 µg of recombinant human GST-SIRT2 (amino acids 18-340) or 0.5 µg of recombinant yeast Sir2p were incubated for 2 hours at 30° C. in 50 µl of assay buffer (50 mm Tris-HCl, pH 8.8, 4 mM $MgCl_2$, 0.2 mM dithiothreitol), with or without 50 µm NAD and acetylated HeLa histories (1000 cpm), purified by acid extraction. HDAC activity was determined by scintillation counting of the ethyl acetate-soluble [$^3$H]acetic acid (Grozinger et al., *J. Biol. Chem.* 276:38837-38843, 2001). Assays that can be used to determine cellular toxicity are also known in the art, as are assays for assessing a compound's ability to promote or inhibit aggregate formation in cells (see, e.g., WO 05/087217, the content of which is hereby incorporated by reference in its entirety). Assays to assess SIRT2 activity are also described in the Examples below.

Any of these assays or any combination of these assays can be used to test (or further test) the present compounds as well as to identify other compounds or moieties, such as proteins (e.g., antibodies) and nucleic acids (e.g., oligonucleotides or molecules that mediate RNAi (e.g., siRNAs or shRNAs)) useful in the diagnosis, prevention, or treatment of a disorder associated with sirtuin (e.g., SIRT2) activity or characterized by an abnormal association of one protein with another. Libraries that encode or contain candidate compounds are available to those of ordinary skill in the art through charitable sources (e.g., ChemBridge Corporation (San Diego, Calif.) (which provides useful information about chemical libraries on the worldwide web)) and commercial suppliers. Sources include Asinex (Moscow, Russia); Bionet (Camelford, England); ChemDiv (San Diego, Calif.); Comgenex (Budapest, Hungary); Enamine (Kiev, Ukraine); IF Lab (Ukraine); Interbioscreen (Moscow, Russia); Maybridge (Tintagel UK); Specs (The Netherlands); Timtec (Newark, Del.); and Vitas-M Lab (Moscow, Russia).

Compounds: We have identified certain compounds, which are categorized according to one of a compound described herein (e.g., compounds of formulae I-X). The invention encompasses these compounds in, for example, a substantially pure form, as well as various compositions containing one or more of them (e.g., pharmaceutical formulations, concentrated stocks, packaged products, and kits) and methods of using them.

While pharmaceutical formulations are described further below, we note here that the present compounds can be formulated for oral or parenteral administration to a patient. Likewise, while methods are described further elsewhere herein, we note that the invention encompasses methods of treating a subject who has, who has been diagnosed as having, or who is at risk of developing, a disorder characterized by undesirable sirtuin activity. The methods can include the step of identifying the subject (or patient) and administering to the subject a therapeutically effective amount of a pharmaceutical composition that includes any of the compounds described herein (e.g., a compound described herein (e.g., compounds of formulae I-X)).

Formula I is:

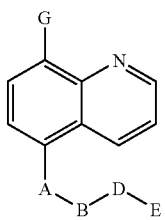

Referring to Formula I, any one or more of A, B and D can be absent. For example, A can be absent or can be S, $NR^1$, $NR^2C(S)NR^3$, or heterocycloalkyl optionally substituted with 1, 2, 3, 4, or 5 halo, OH, CN, or $C_{1-6}$ alkyl. B can be absent, $C_{1-6}$ alkylenyl, $C_{2-6}$ alkenylenyl, $C_{2-6}$ alkynylenyl, O—$C_{1-6}$ alkylenyl, aryl, heteroaryl, or $S(O)_2$, and the $C_{1-6}$ alkyl, $C_{2-6}$ alkenyl, $C_{2-6}$ alkynyl, O—$C_{1-6}$-(alkylenyl, aryl, or heteroaryl can be optionally substituted with 1, 2, 3, or 4 oxo, CN, OH, halo, aryl, or heteroaryl. D can be absent, $C_{1-6}$ alkylenyl, $C_{2-6}$ alkenylenyl, $C_{2-6}$ alkynylenyl, O—$C_{1-6}$ alkylenyl, aryl, heteroaryl, or heterocyclyl, and the $C_{1-6}$ alkylenyl, $C_{2-6}$ alkenylenyl, $C_{2-6}$ alkynylenyl, O—$C_{1-6}$ alkylenyl, aryl, heteroaryl, or heterocyclyl can be optionally substituted with 1, 2, or 3 of $C_{1-6}$ alkyl, halo, OH, aryl, or heteroaryl. E can be H, aryl, heterocyclyl, or heteroaryl, and the aryl or heteroaryl can be optionally substituted with 1, 2, 3, 4, or 5 halo, OH, CN, $C_{1-6}$ alkyl. E can also be halo, OH, CN, or $C_{1-6}$ alkyl. G can be H, $NR^4R^5$, or $NO_2$. $R^1$, $R^2$, and $R^3$ can each be, independently, H, $C_{1-6}$ alkyl, or $C_{1-6}$ haloalkyl, and $R^4$ and $R^5$ can each be, independently, H, $C_{1-6}$ alkyl, or $C_{1-6}$ haloalkyl.

Under physiological conditions (e.g. in vivo), compounds of Formula I can inhibit an activity of a sirtuin (e.g., SIRT2).

In other embodiments, A can be $NR^1$. When A is $NR^1$, $R^1$ can be H. Alternatively, or in addition, G can be H and/or B can be $C_3$ alkenylenyl. Where an alkenylenyl is substituted, the substitution can be with oxo. Where an alkenylenyl (e.g., $C_3$ alkenylenyl) is present (e.g., at the position represented by B), the alkenylenyl can be further substituted with CN. In any of the compounds described herein by Formula I, D can be heteroaryl, which can include O. In any of the compounds described herein by Formula I, E can be aryl, and the aryl can be substituted with at least one halo (e.g., two halo). For example, the halo can be at least one (e.g., two) of chloro/chlorine, fluoro/fluorine, bromo/bromine or iodo/iodine.

In other embodiments, the compounds (e.g., substantially pure compounds) can be compounds of Formula I in which G is $NO_2$. Alternatively, or in addition, B can be heteroaryl (e.g., a heteroaryl that includes N). The heteroaryl can be substituted with aryl (e.g., phenyl). In these embodiments and others, P can be O—$C_1$ alkylenyl and/or E can be aryl (e.g., phenyl).

In other embodiments, in a compound conforming to Formula I, A can be S. Alternatively, or in addition, in a compound conforming to Formula I, one or more of the following requirements is satisfied: C is $NO_2$; B is heteroaryl (e.g., a heteroaryl comprising N or a heteroaryl substituted with aryl (e.g., phenyl)); D is O—$C_1$ alkylenyl; and E is aryl (e.g., phenyl).

Formula II is:

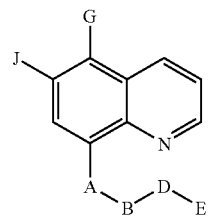

Referring to Formula II, any one or more of A, B, and D can be absent. A can also be S, $NR^1$, $NR^2C(S)NR^3$, or heterocycloalkyl optionally substituted with 1, 2, 3, 4, or 5 halo, OH, CN, or $C_{1-6}$ alkyl. B can be absent, $C_{1-6}$ alkylenyl, $C_{2-6}$ alkenylenyl, $C_{2-6}$ alkynylenyl, O—$C_{1-6}$ alkylenyl, aryl, heteroaryl or $S(O)_2$, wherein the $C_{1-6}$ alkyl, $C_{2-6}$ alkenyl, $C_{2-6}$ alkynyl, O—$C_{1-6}$ alkylenyl, aryl or heteroaryl is optionally substituted with 1, 2, 3, or 4 oxo, CN, OH, halo, aryl or heteroaryl. D can be absent, $C_{1-6}$ alkylenyl, $C_{2-6}$ alkenylenyl, $C_{2-6}$ alkynylenyl, O—$C_{1-6}$ alkylenyl, aryl heteroaryl, or heterocyclyl, and the $C_{1-6}$ alkylenyl, $C_{2-6}$ alkenylenyl, $C_{2-6}$ alkynylenyl, $C_1$ O—$C_{1-6}$ alkylenyl, aryl, heteroaryl, or heterocyclyl is optionally substituted with 1, 2, or 3 $C_{1-6}$ alkyl, halo, OH, aryl, or heteroaryl. E can be H, aryl, heterocyclyl, or heteroaryl, and the aryl, or heteroaryl is optionally substituted with 1, 2, 3, 4, or 5 halo, OH, CN, or $C_{1-6}$ alkyl. G can be H, $NR^4R^5$, or $NO_2$. J can be H or OH. $R^1$, $R^2$, and $R^3$ are each, independently, H, $C_{1-6}$ alkyl, or $C_{1-6}$ haloalkyl, and $R^4$ and $R^5$ are each, independently, H, $C_{1-6}$ alkyl, or $C_{1-6}$ haloalkyl.

Under physiological conditions (e.g. in vivo), compounds of Formula II can inhibit an activity of a sirtuin (e.g., SIRT2).

Formula III is:
Formula III is:

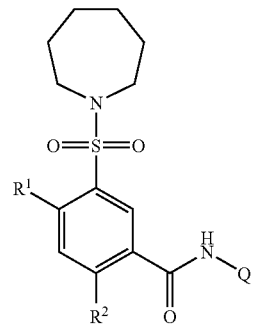

Referring to Formula III, Q can be Cy or —($C_{1-6}$ alkyl)-Cy, and Cy or —($C_{1-6}$ alkyl)-Cy can be optionally substituted by 1, 2, 3, 4, or 5 substituents individually selected from halo, $C_{1-10}$ alkyl, aryl, $C_{1-10}$ haloalkyl, CN, $NO_2$, oxo, $OR^{a1}$, $C(O)OR^{a2}$, $SO_2R^{a3}$, and $SR^{b1}$;

$R^1$ can be H, halo, or $C_{1-10}$ alkyl;

$R^2$ can be H, halo, or $C_{1-10}$ alkyl;

Cy can be cycloalkyl, 4-20 membered heterocycloalkyl, aryl, or heteroaryl;

$R^{a1}$ can be H or $C_{1-10}$ alkyl;

$R^{a2}$ can be H or $C_{1-10}$ alkyl;

$R^{a3}$ can be $C_{1-10}$ alkyl; and $R^{b1}$ can be $C_{1-10}$ alkyl.

In other embodiments, Q can be phenyl, and the phenyl moiety can be optionally substituted by 1, 2, 3, 4, or 5 substituents independently selected from halo, $C_{1-6}$ alkyl, $C_{1-6}$ haloalkyl, $NO_2$, $OR^{a1}$, and $C(O)OR^{a2}$.

In other embodiments, Q can be heteroaryl, and the heteroaryl can be optionally substituted by 1, 2, 3, 4, or 5 substituents individually selected from halo, $C_{1-6}$ alkyl, aryl, $C(O)OR^{a1}$, $SO_2R^{a3}$, and $SR^{b1}$.

In other embodiments, Q can be heterocycloalkyl, and the heterocycloalkyl can be optionally substituted by 1, 2, 3, 4, or 5 substituents independently selected from CN, oxo, and $C(O)OR^{a2}$.

In other embodiments, Q can be —($C_{1-6}$ alkyl)-heterocycloalkyl, and the —($C_{1-6}$ alkyl)-heterocycloalkyl can be —($C_{1-6}$ alkyl)-morpholino.

In other embodiments, Q can be —($C_{1-6}$ alkyl)-heteroaryl, and the —($C_{1-6}$ alkyl)-heteroaryl can be —($C_{1-6}$ alkyl)-furan.

In any embodiment of Formula III, $R^1$ can be H, bromo, or methyl. Alternatively, or in addition, $R^2$ can be H or chloro.

In certain embodiments, a compound conforming to Formula III can be:

3-(azepane-1-sulfonyl)-N-(3-nitro-phenyl)-benzamide;
3-(azepane-1-sulfonyl)-N-(3-bromo-phenyl)-benzamide;
3-(azepane-1-sulfonyl)-4-bromo-N-(3-nitro-phenyl)-benzamide;
3-(azepane-1-sulfonyl)-N-(3-trifluoromethyl-phenyl)-benzamide;
3-(azepane-1-sulfonyl)-N-(2,4-dimethyl-phenyl)-benzamide,
3-(azepane-1-sulfonyl)-N-(4-methyl-pyridin-2-yl)-benzamide;
3-(azepane-1-sulfonyl)-N-pyridin-2-yl-benzamide;
3-(azepane-1-sulfonyl)-N-(5-chloro-pyridin-2-yl)-benzamide;
3-(azepane-1-sulfonyl)-N-(3-cyano-4,5,6,7-tetrahydrobenzo[b]thiophen-2-yl)-benzamide;
3-(azepane-1-sulfonyl)-N-benzothiazol-2-yl-benzamide;
3-(azepane-1-sulfonyl)-N-(6-methanesulfonyl-benzothiazol-2-yl)-benzamide;
3-(azepane-1-sulfonyl)-N-(5-phenyl-thiazol-2-yl)-benzamide;
2-[3-(azepane-1-sulfonyl)-benzoylamino]-4,5-dimethyl-thiophene-3-carboxylic acid ethyl ester;
2-[3-(azepane-1-sulfonyl)-benzoylamino]-4,5,6,6a-tetrahydro-3aH-cyclopenta[b]thiophene-3-carboxylic acid ethyl ester;
3-(azepane-1-sulfonyl)-N-(1,1-dioxo-tetrahydro-1$\Sigma^6$-thiophen-3-yl)-benzamide;
3-(azepane-1-sulfonyl)-N-(2-morpholin-4-yl-ethyl)-benzamide;
3-(azepane-1-sulfonyl)-N-(5-methyl-isoxazol-3-ylmethyl)-benzamide;
3-(azepane-1-sulfonyl)-N-isoxazol-3-ylmethyl-benzamide;
3-(azepane-1-sulfonyl)-N-benzo[1,3]dioxol-5-yl-benzamide;
3-(azepane-1-sulfonyl)-N-(2,3-dihydro-benzo[1,4]dioxin-6-yl)-benzamide;
3-(azepane-1-sulfonyl)-N-furan-2-ylmethyl-benzamide;
3-(azepane-1-sulfonyl)-N-(4-methoxy-phenyl)-benzamide;
3-(azepane-1-sulfonyl)-N-phenyl-benzamide;
3-(azepane-1-sulfonyl)-N-cycloheptyl-benzamide;
2-[3-(azepane-1-sulfonyl)-4-methyl-benzoylamino]-benzoic acid;
3-(azepane-1-sulfonyl)-N-benzo[1,3]dioxol-5-yl-4-methyl-benzamide;
3-(azepane-1-sulfonyl)-N-isoxazol-3-yl-4-methyl-benzamide;
3-(azepane-1-sulfonyl)-4-methyl-N-(5-methylisoxazol-3-yl)-benzamide;
3-(azepane-1-sulfonyl)-N-(1,1-dioxo-tetrahydro-1$\Sigma^6$-thiophen-3-yl)-4-methyl-benzamide;
2-[3-(azepane-1-sulfonyl)-4-methyl-benzoylamino]-4,5,6,6a-tetrahydro-3aH-cyclopenta[b]thiophene-3-carboxylic acid ethyl ester;
2-[3-(azepane-1-sulfonyl)-4-methyl-benzoylamino]-4,5-dimethyl-thiophene-3-carboxylic acid ethyl ester;
3-(azepane-1-sulfonyl)-4-methyl-N-thiazol-2-yl-benzamide;
3-(azepane-1-sulfonyl)-4-methyl-N-(5-methylsulfany-[1,3,4]thiadiazol-2-yl)-benzamide;
3-(azepane-1-sulfonyl)-4-methyl-N-(5-methyl-[1,3,4]thiadiazol-2-yl)-benzamide;
3-(azepane-1-sulfonyl)-4-bromo-N-(3-hydroxy-phenyl)-benzamide;
3-(azepane-1-sulfonyl)-N-(3-hydroxy-phenyl)-4-methyl-benzamide; and
5-(azepane-1-sulfonyl)-2-chloro-N-(3-hydroxy-phenyl)-benzamide, or
pharmaceutically acceptable salt thereof.

The following definitions apply to the terms used in connection with any of the formulas herein. As used herein, the term "alkyl" is meant to refer to a saturated hydrocarbon group which is straight-chained or branched. Exemplary alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20 carbon atoms (e.g., from 2 to about 20, from 1 to about 10, from 1 to about 8, from 1 to about 6, from 1 to about 4, or from 1 to about 3 carbon atoms).

As used herein, "alkenyl" refers to an alkyl group having one or more double carbon-carbon bonds. Example alkenyl groups include ethenyl, propenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Exemplary haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to a non-aromatic heterocycle where one or more of the ring-forming atoms is a heteroatom such as an O, N, or S atom. Heterocycloalkyl groups can include mono- or polycyclic (e.g., having 2, 3 or 4 fused rings) ring systems as well as spirocycles. Exemplary "heterocycloalkyl" groups include morpholhno, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

It is understood that when a substituent is depicted structurally as a linking moiety, it is necessarily minimally divalent. For example, when the variable $R^{3a}$ of the structure depicted in Formula I is alkyl, the alkyl moiety is understood to be an alkyl linking moiety such as —$CH_2$—, —$CH_2CH_2$—, $CH_3CH$<, etc.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods for preparing optically active forms from optically active starting materials are known in the art, such as by resolution of racemnic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention also include tautomeric forms, such as keto-enol tautomers.

Compounds of the invention can also include all isotopes of atoms occurring in the intermediates or final compounds. Isotopes include those atoms having the same atomic number but different mass numbers. For example, isotopes of hydrogen include tritium and deuterium.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Pharmaceutically acceptable compounds are those compounds (including materials, compositions, and/or dosage forms) that are, within the scope of sound medical judgment, suitable for use in contact with the tissues of human beings and animals without excessive toxicity, irritation, allergic response, or other problem or complication, commensurate with a reasonable benefit:risk ratio.

Salts, solvates, and other variants: The invention also encompasses pharmaceutically acceptable salts or solvates of a compound of any of Formulas I-X and prodrugs, metabolites, structural analogs, and other pharmaceutically or experimentally useful variants thereof. These other variants may be, for example, complexes containing the compound and a targeting moiety, as described further below, a second therapeutic agent or a detectable marker (e.g., the compound may incorporate a radioactive isotope or be joined to a fluorescent compound). When in the form of a prodrug, a compound is modified in vivo (e.g., intracellularly) after being administered to a patient or to a cell in culture. The modified compound (i.e., the processed prodrug) may be identical to a compound described herein and will be biologically active or have enough activity to be clinically beneficial.

A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

Examples of prodrugs include esters and other pharmaceutically acceptable derivatives, which, upon administration to a subject, are capable of providing active compounds. Thus, a prodrug can be any pharmaceutically acceptable salt, ester, salt of an ester, or other derivative of a present compound (for example an imidate ester of an amide), which, upon administration to a recipient, is capable of providing (directly or indirectly) a present compound. Particularly favored derivatives and prodrugs are those that increase the bioavailability of a compound after it is administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to the compounds described herein.

The present compounds can be modified by appending appropriate functionalities to enhance selected biological properties (e.g., targeting to a particular tissue). Such modifications are known in the art and include those that increase biological penetration into a given biological compartment (e.g., blood, lymphatic system, central nervous system), increase oral availability, increase solubility to allow administration by injection, alter metabolism, or alter (e.g., slow) the rate of excretion.

The present compounds can contain one or more asymmetric centers and thus occur as racemates and racemic mixtures, single enantiomers, individual diastereomers and diastereomeric mixtures. All such isomeric forms of these compounds are expressly included in the present invention. The present compounds may also contain linkages (e.g., carbon-carbon bonds) wherein bond rotation is restricted about that particular linkage (e.g., restriction resulting from the presence of a ring or double bond). Accordingly, all cis/trans and E/Z isomers are expressly included in the present invention. The present compounds may also be represented in multiple tautomeric forms, and in such instances, the invention expressly includes all tautomenc forms of the compounds described herein, even though only a single tautomerc form may be represented (e.g., alkylation of a ring system may result in alkylation at multiple sites, and the invention expressly includes all such reaction products). All such isomeric forms of such compounds are expressly included in the present invention. All crystal forms of the compounds described herein are expressly included in the present invention.

As noted, the present compounds can be mixed with or joined to a detectable marker or tag, to another therapeutic agent, or to a moiety that facilitates passage across the blood-brain barrier (see below).

Packaged products: The compounds described herein can be packaged in suitable containers labeled, for example, for use as a therapy to treat a disorder associated with sirtuin activity (e.g., Parkinson's Disease). The containers can include the compound (i.e., the diagnostic/prophylactic/therapeutic agent) and one or more of a suitable stabilizer, carrier molecule, flavoring, and/or the like, as appropriate for the intended use. Accordingly, packaged products (e.g., sterile containers containing one or more of the compounds described herein and packaged for storage, shipment, or sale at concentrated (e.g., lyophilized) or ready-to-use concentrations) and kits, including at least one of the present compounds and instructions for use, are also within the scope of the invention. A product can include a container (e.g., a vial, jar, bottle, bag, or the like) containing one or more of the present compounds and a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefore, and other uses. The compounds can be ready for administration (e.g., present in dose-appropriate units), and may include a pharmaceutically acceptable adjuvant, carrier or other diluent and/or an additional therapeutic agent. Alternatively, the compounds can be provided in a concentrated form with a diluent and instructions for dilution.

Stability: Combinations of substituents and variables envisioned by this invention are only those that result in the formation of stable compounds. The term "stable," as used herein, refers to compounds that are stable enough to allow manufacture and that maintain their integrity for a sufficient period of time to be useful for the purposes detailed herein (e.g., therapeutic or prophylactic administration to a subject).

Purity: In one aspect, the invention features substantially pure preparations of the compounds described herein or combinations thereof. A naturally occurring compound is substantially pure when it is separated to some degree from the compound(s) or other entities (e.g., proteins, fats, or minerals) it is associated with in nature. For example, a naturally occurring compound described herein is substantially pure when it has been separated from 50%, 60%, 70%, 75%, 80%, 85%, 90%, 95%, 96%, 97%, 98%, 99% or more of the compound(s) or other moieties it is associated with in nature. These degrees of purity are not limiting, however. The compounds of the invention need be only as pure as necessary to cause a beneficial clinical result and to conform with good manufacturing practices. While the compounds of the invention may be naturally occurring and may be purified using conventional techniques, they may also be non-naturally occurring and may be synthesized (naturally occurring compounds can be synthesized as well; see below). Compounds prepared by chemical synthesis are substantially pure, as are compounds that have been separated from a library of chemical compounds. A substantially pure compound may be one that is separated from all the other members of the compound library or it may be one that has been separated to a limited extent (e.g., it may remain associated with a limited number (e.g., 1, 2, 3, 4, or 5-10) of other members of the library. As noted, while more than one of the agents described herein can be formulated within the same composition, and while the compositions can also include a second therapeutic agent (as described herein), the pharmaceutical compositions of the invention expressly exclude extremely heterogeneous mixtures, such as libraries (e.g., combinatorial or compound libraries, including those that contain synthetic and/or natural products, and custom analog libraries, which may contain compounds based on a common scaffold). Such libraries can include hundreds or thousands of distinct compounds or random pools thereof. Whether or not commercially available, such libraries are excluded from the meaning of a pharmaceutical composition.

Formulations. Regardless of their original source or the manner in which they are obtained, the present compounds can be formulated in accordance with their use. For example, the compounds can be formulated within compositions for application to cells in tissue culture or for administration to a patient. For example, the compounds can be mixed with a sterile, pharmaceutically acceptable diluent (such as normal saline). As noted below, and as known in the art, the type of diluent can vary depending upon the intended route of administration. The resulting compositions can include additional agents, such as preservatives. The compounds may also be applied to a surface of a device (e.g., a catheter) or contained within a pump, patch, or other drug delivery device. The present compounds (or research or therapeutic agents) can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E. W. Martin), a well-known reference text in this field, and in the USP/NF (United States Pharmacopeia and the National Formularly).

A pharmaceutical composition (e.g., a composition containing one or more of the present compounds) is formulated to be compatible with its intended route of administration. Examples of routes of administration include oral, rectal, and parenteral, for example, intravenous, intradermal, and subcutaneous, transdermal (topical), and transmucosal administration. While inconvenient, the present compounds can be administered through a pump, catheter, or other device directly to the central nervous system. Variants of the compounds described herein, formulated to cross the blood-brain barrier, are described below.

Diagnostic, prophylactic and therapeutic use: The compounds described here (which may also be referred to as "therapeutic agents") may be used to treat a variety of disorders associated with undesirable sirtuin (e.g., SIRT2) activity, including Parkinson's Disease.

Treating a subject can encompass administration of a therapeutic agent as a prophylactic measure to prevent the occurrence of a disorder, to lessen the severity or duration of the symptoms associated with the disorder, or to prolong the time or severity of onset. Physicians and others of ordinary skill in the art routinely make determinations as to the success or failure of a treatment. Treatment can be deemed successful despite the fact that not every symptom of the disorder is totally eradicated. Treatment can also be deemed successful despite side-effects.

It is usual in the course of developing a therapeutic agent that tests of that agent in vitro or in cell culture are followed by tests in animal models of human disease, and further, by clinical trials for safety and efficacy in humans. Accepted animal models for many disorders are now known to those of ordinary skill in the art. For example, therapeutic agents of the present invention can be screened in a *Drosophila* model of neurodegeneration as well as in more evolutionarily advanced animals. For example, mammalian models for Huntington's disease are available.

In specific embodiments, the compositions of the present invention can be administered to a subject having any disease mediated by (or characterized by) an abnormal level of sirtuin activity. A compound described herein (e.g., compounds of formulae I-IX) can be used in methods of treating a subject, including a human patient (e.g., a human patient who has been diagnosed as having a disorder associated with expression of a sirtuin). More specifically, the methods can be carried out by identifying a subject who has been diagnosed as having, or who is at risk of developing, a disorder that is associated with, or mediated at least in part by, a sirtuin and administering to the subject a therapeutically effective amount of a pharmaceutical composition described herein (e.g., a pharmaceutical composition that includes a compound as described herein). The subject can be a subject (or "patient") diagnosed as having, or one who is at risk of developing, a neoplastic disorder characterized by unwanted cellular proliferation; a neurological disorder; a disorder prevalent in the elderly; or a metabolic disorder. More specifically, disorders characterized by unwanted cellular proliferation include cancer (e.g., breast cancer, neuroblastoma, myeloma, or any cancer associated with loss of the tumor suppressor p53) and non-malignant growths. Because of our current understanding of cellular mechanisms, we also believe that the compounds described here can be used to treat the cancers for which paclitaxel (Taxol™) is currently prescribed. In addition to breast cancers, these include ovarian cancers, lung cancers (e.g., non-small cell lung cancer), and Kaposi's sarcoma. Disorders classified as neurological disorders include Huntington's disease (an aggregation associated disease), Parkinson's disease, Alzheimer's disease, spinal and bulbar muscular atrophy, dentatorubral-pallidoluysian atrophy, spinocerebellar ataxia type 1 (SCA1), SCAM, SCA6, SCA7, Machado-Joseph disease (MJD/SCA3), and Creutzfeldt-Jakob disease. Disorders prevalent in the elderly include dementia, osteoporosis, hypertension, unsteady gait and difficulty maintaining balance. The present compounds can also benefit and can be administered to adult and elderly patients generally, whether or not they have a disorder associated with aging. When administered to adult or elderly patients that do not have a disorder associated with a sirtuin, the compounds may benefit the patient by inhibiting the onset of a condition associated with aging, by reducing the risk of cancer, or by generally promoting better health (e.g. as is likely to occur when a patient is able to maintain an ideal weight or blood pressure) and/or longevity. The metabolic disorders include amyloidosis, alpha-1-antitrypsin deficiency disease, diabetes (e.g., type I or type II diabetes), metabolic syndrome, and atherogenic dyslipidemia. A present compound can also be used to treat subjects who are overweight or obese. A present compound can also be used to treat a subject who is experiencing, or may experience, complications during chronic renal dialysis. Inhibitors of histone deacetylase inhibitors induce hyperacetylation of histones that modulate chromatin structure and gene expression. These inhibitors also induce growth arrest, cell differentiation, and apoptosis of tumor cells (Moreira, BMC Cancer 3:30, 2003).

Other patients amenable to treatment are those identified as having, or at risk of developing, immunoglobulin light chain amyloidosis, diabetes (e.g., juvenile- or adult-onset diabetes), cirrhosis (e.g., cirrhosis of the liver), emphysema, or a prion disease.

One of ordinary skill in the art would understand that the categorizations set out here are not absolute; one disorder or condition may be suitably categorized in more than one category. For example, PD and AD may be accurately described as either neurological disorders or as disorders associated with aging. Age is considered a major risk factor for developing PD or AD.

Subjects who are treated with the compounds of the invention may have been diagnosed with any disorder associated with undesirable sirtuin activity, whether that activity occurs to a greater or lesser extent than is normal (m, e.g., a healthy patient) or desirable. Alternatively, the subject may be at risk for developing these disorders. For example, a subject may have a family history or a genetic mutation or element that contributes to the development of a disorder described herein. Human subjects, in consult with their physicians and/or other health care professionals, can decide whether their risk is great enough to undergo preventative care (as is the case for any prophylactic treatment or procedure). While the subjects of the preventative and/or therapeutic regimes described herein may be human, the compounds and compositions of the invention can also be administered to non-human subjects.

The prophylactic and therapeutic methods can be carried out by administering to the subject a pharmaceutical composition containing a therapeutically effective amount of one or more of the compounds described herein. While a single compound may be effective, the invention is not so limited. A subject can be treated with multiple compounds, administered simultaneously or sequentially. For example, a subject can be treated with one or more of the compounds described herein and, optionally, a chemotherapeutic agent, an analgesic, a bronchodilator, levodopa or a similar medication. The combination therapy will, of course, depend on the disorder being treated. Where a compound of the invention is administered to treat a patient with a cancer, it may be combined with a known chemotherapeutic agents used to treat that type of cancer; where a compound of the invention is administered to treat a patient with Parkinson's disease, it may be combined with a medication to increase dopamine levels in the brain; and so forth.

The blood-brain barrier is an obstacle for the delivery of drugs from circulation in the bloodstream to the brain. The endothelial cells of brain capillaries are connected by tight intercellular junctions, which inhibit the passive movement of compounds out of the blood plasma into the brain. These cells also have reduced pinocytic vesicles in order to restrict the indiscriminate transport of materials intracellularly. These features of the brain regulate the exchange of materials between plasma and the central nervous system. Both active and passive transport mechanisms operate to exclude certain molecules from traversing the barrier. For example, lipophilic compounds are more permeable to the barrier than hydrophilic compounds (Goldstein et al., Scientific American 255: 74-83, 1996; Pardridge et al., Endocrin. Rev. 7:314-330, 1996).

However, the blood-brain barrier must also allow for the selective transport of desired materials into the brain in order to nourish the central nervous system and to remove waste products. The mechanisms by which this is accomplished can provide the means for supplying the therapeutic agents described herein.

The present compositions can be delivered to the CNS following conjugation with other compounds as follows (and as described further in, for example, U.S. Pat. No. 5,994,392). In one instance, polar groups on a compound are masked to generate a derivative with enhanced lipophilic qualities. For example, norepinephrine and dopamine have been modified with diacetyl and triacetyl esters to mask hydroxyl groups. An implementation of this strategy has been previously used to create a pro-drug derivative of dopamine (see U.S. Pat. No. 5,994,392). The modified drugs are generally referred to as pro-drugs, and the compounds of the invention encompass those described herein in which polar groups are masked. This method may have the additional advantage of providing an inactive species of the compound in the general circulation. After crossing the blood-brain barrier, enzymes present in the central nervous system are able to hydrolyze the linkages (e.g., ester linkages), thereby unmasking the compound and liberating the active drug. Thus, compounds of the invention can be chemically modified to create pro-drugs by, e.g., conjugation to a lipophilic moiety or carrier. A compound or a variant thereof having at least one free hydroxyl or amino group can be coupled to a desired carrier (e.g., a fatty acid, a steroid, or another lipophilic moiety).

More specifically, and for example, the hydroxyl groups can first be protected with acetonide. The protected agent is then reacted with the desired carrier in the presence of a water-extracting compound (e.g., dicyclohexyl carbodiiamide), in a solvent (e.g., dioxane, tetrahydrofurane), or N,N dimethylformamide at room temperature. The solvent is then removed, and the product is extracted using methods routinely used by those of ordinary skill in the art. Amine groups can be coupled to a carboxyl group in the desired carrier. An amide bond is formed with an acid chloride or low carbon ester derivative of the carrier. Bond formation is accompanied by HCl and alcohol liberation. Alcohol groups on the compound can be coupled to a desired carrier using ester bonds by forming an anhydride derivative, i.e. the acid chloride derivative, of the carrier. One of ordinary skill in the art of chemistry will recognize that phosphoramide, sulfate, sulfonate, phosphate, and urethane couplings are also useful for coupling a therapeutic agent (e.g., a compound described herein) to a desired carrier. A useful and adaptable method for lipidation of antibodies is described by Cruikshank et al. (*J. Acquired Immune Deficiency Syndromes and Human Retrovirology* 4:193, 1997).

Procedures for delivering therapeutic agents (or "compounds") of the invention to the CNS can also be carried out using the transferrin receptor as described, for example, in U.S. Pat. No. 6,015,555. To implement this procedure, the agents are conjugated to a molecule that specifically binds to the transferrin receptor (e.g., an antibody or antigen-binding fragment thereof, or transferrin). Methods for obtaining antibodies against the transferrin receptor and for coupling the antibodies to a desired compound are also described in U.S. Pat. No. 6,015,555.

Monoclonal antibodies that specifically bind to the transferrin receptor include OX-26, T58/30, and B3/25 (Omary et al., *Nature* 286:888-891, 1980), T56/14 (Gatter et al., *J. Clin. Path.* 36:539-545, 1983), OKT-9 (Sutherland et al., *Proc. Natl. Acad. Sci. USA* 78:4515-4519, 1981), L5.1 (Rovera, *Blood* 59:671-678, 1982) and 5E-9 (Haynes et al., *J. Immunol.* 127:347-351, 1981). In one embodiment the monoclonal antibody OX-26 is used. The antibody of choice can be an Fab fragment, a F(ab')$_2$ fragment, a humanized antibody, a chimeric antibody, or a single chain antibody.

The antibody to the transferrin receptor is conjugated to a desired compound with either a cleavable or non-cleavable linker. The preferred type of linker can be determined without undue experimentation by making cleavable and non-cleavable conjugates and assaying their activity in, for example, an in vitro or cell culture assay described herein. The conjugates can be further tested in vivo (e.g., in a animal model of a disease of interest). Examples of chemical systems for generating non-cleavable linkers include the carbodiimmide, periodate, sulfhydryl-maleimide, and N-succinimidyl-3-(2-puridyldithio) propionate (SPDP) systems. Carbodiimide activates carboxylic acid groups, which then react with an amino group to generate a noncleavable amide bond. This reaction may be especially useful for coupling two proteins. Penrodate is used to activate an aldehyde on an oligosaccharide group such that it can react with an amino group to generate a stable conjugate. Alternatively, a hydrazide derivative of the desired compound can be reacted with the antibody oxidized with periodate. Sulfhydryl-maleimide and SDPD use sulfiydryl chemistry to generate non-cleavable bonds. SDPD is a heterobifunctional crosslinker that introduces thiol-reactive groups. In the sulfhydryl-maleimide system, an NHS ester (e.g., gannma-maleimidobutyric acid NHS ester) is used to generate maleimide derivative, for example, of a protein drug or antibody. The maleimide derivative can react with a free sulfhydryl group on the other molecule.

Cleavable linkers are also useful. Cleavable linkers include acid labile linkers such as cis-aconitic acid, cis-carboxylic alkadienes, cis-carboxylic alkatrienes, and polypeptide-maleic anhydrides (see U.S. Pat. No. 5,144,011).

A present compound can be covalently attached to an antibody specific for the transferrin receptor. In one embodiment, use of a single chain antibody is preferred in order to facilitate covalent fusion with the therapeutic agent.

The targeting antibody can be linked covalently to the therapeutic agent (or "compound") of the invention. A protease recognition site can be included in the linker if cleavage of the antibody is required after delivery.

The efficacy of strategies to deliver a desired compound across the blood-brain barrier can, of course, be monitored. The desired compound, conjugated for delivery across the blood-brain barrier, is administered to a test mammal (e.g., a rat, a mouse, a non-human primate, a cow, a dog, a rabbit, a cat, or a sheep). One of ordinary skill in the art will, however, recognize that the permeability of the blood-brain barrier varies from species to species, with the human blood-brain barrier being the least permeable. The mode of administration can be the same as the desired mode of treatment (e.g., intravenous). For a comprehensive analysis, a set of test mammals is used. The test mammals are sacrificed at various times after the agent is administered and are then perfused through the heart with, e.g., Dulbecco's phosphate-buffered saline (DPBS) to clear the blood from all organs. The brain is removed, frozen in liquid nitrogen, and subsequently sectioned in a cryostat. The sections are placed on glass microscope slides. The presence of the desired agent is then detected in the section, for example with an antibody, or by having administered a radiolabeled or otherwise tagged compound (such labeled therapeutic compounds as described above). Detection is indicative of the compound having successfully traversed the blood-brain barrier. If a method of enhancing the compounds permeability to the blood-brain barrier is being assessed, then the amount of the agent detected in a brain section can be compared to the amount detected in a brain section from an animal treated with the same compound without the enhancing method.

The terms "blood-brain barrier permeant" or "blood-brain barrier permeable" are qualities of a compound for which the ratio of a compound's distribution at equilibrium in the cerebrospinal fluid (CSF) relative to its distribution in the plasma (CSF/plasma ratio) is greater than at least (or about) 0.01, 0.02, 0.05, or 0.1. While lower ratios are generally preferred, any ratio that allows a compound to be used clinically is acceptable.

To facilitate targeting, a compound (e.g., a compound conforming to any of Formulas I, II, or III) can include a moiety that specifically binds to the target protein. For example, a compound conforming to Formula I can be joined to an antibody or an antigen-binding portion thereof (e.g., a single chain antibody) that specifically binds the target protein (e.g., SIRT2).

A therapeutic vector can be administered to a subject, for example, by intravenous injection, by local administration (see U.S. Pat. No. 5,328,470) or by stereotactic injection (see e.g., Chen et al., *Proc. Nart Acad. Sci. USA* 91:3054-3057, 1994). The compound can be further formulated, for example, to delay or prolong the release of the active agent by means of a slow release matrix.

Regardless of whether or not the compound is to cross the blood-brain barrier, it can be conjugated to a targeting agent that facilitates interaction with a target protein (e.g., SIRT2). As noted, the compound can be directly or indirectly joined to an antibody (e.g., a single chain antibody) or an antigen-binding fragment thereof that specifically binds the target protein.

An appropriate dosage of the therapeutic agents of the invention must be determined. An effective amount of a therapeutic compound is the amount or dose required to ameliorate a symptom of a disorder associated with protein aggregation, such as a disorder characterized by a trinucleotide repeat expansion. Determining the amount required to treat a subject is routine to one of ordinary skill in the art (e.g., a physician, pharmacist, or researcher). First, the toxicity and therapeutic efficacy of an agent (i.e. a tri-domain molecule) is determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Compounds, formulations, and methods of administration with high therapeutic indices are preferable as such treatments have little toxicity at dosages that provide high efficacy. Compounds with toxic or undesirable side effects can be used, if means are available to deliver the compound to the affected tissue, while minimizing damage to unaffected tissue.

In formulating a dosage range for use in humans, the effective dose of a therapeutic agent can be estimated from in vitro cell studies and in vivo studies with animal models. If an effective dose is determined for ameliorating a symptom in cell culture, a dose can be formulated in an animal in order to achieve a circulating plasma concentration of sodium butyrate that falls in this range. An exemplary dose produces a plasma concentration that exceeds the $IC_{50}$ (i.e., the concentration of the test compound which achieves a half-maximal inhibition of symptoms) as determined in cell culture assays. The circulating plasma concentration can be determined, for example, by administering a labeled therapeutic composition to the test animal, obtaining a blood sample, and quantitating the amount of labeled compound present at various times after administration.

An appropriate daily dose of a therapeutic agent can be between about 0.1 mg/kg of body weight to about 500 mg/kg (e.g., between about 1 mg/kg to about 50 or 100 mg/kg). The dose can be adjusted in accordance with the blood-brain barrier permeability of the compound. For example, a therapeutic compound can be administered at a dosage of 50 mg/kg to 100 mg/kg in order to treat the brain. The dose for a patient can be optimized while the patient is under care of a physician, pharmacist, or researcher. For example, a relatively low dose of a sirtuin inhibitor can be administered initially. The patient can be monitored for symptoms of the disorder being treated (e.g., PD). The dose can be increased until an appropriate response is obtained. In addition, the specific dose level for any particular subject can vary depending on the age, body weight, general health, gender, and diet of the subject, the time of administration, the route of administration, the rate of excretion, and other drugs provided in combination.

As occurs in the course of all drug development, optimal treatment regimes will emerge through further modeling and clinical trials. It may be, for example, that a patient will receive a combination of compounds that act synergistically to inhibit polypeptide association by the same or different mechanisms of action. Combination therapies may also rely on administration of a compound that interferes with gene transcription (e.g., a small molecule or a nucleic acid that mediates RNAi) and a compound that facilitates degradation of any remaining unwanted polypeptide-containing complexes.

The efficacy of a dose of any therapeutic agent can be determined in a subject. For example, the subject can be monitored for clinical symptoms, for example, a symptom of PD or HD. Behavioral symptoms of HD include irritability, apathy, lethargy, depression, hostile outbursts, loss of memory and/or judgment, loss of ability to concentrate, anxiety, slurred speech, difficulty swallowing and/or eating, and inability to recognize persons. Clinical symptoms of HD include loss of coordination, loss of balance, inability to walk, uncontrolled movements of the fingers, feet, face, and/or trunk, rapid twitching, tremors, chorea, rigidity, and akinesia (severe rigidity). Similar symptoms, including tremor, occur in PD patients.

Methods of making: The compounds of the invention or biologically active variants thereof (e.g., salts) may be synthesized in vitro, produced in vivo (e.g., produced within the body (e.g., intracellularly) following administration to a patient), or produced following application to a cell in culture. Accordingly, the present invention features methods of making the compounds and compositions of the present invention.

The compounds can be synthesized using routine techniques known to one of ordinary skill in the art. For example, the compounds can be made by providing a starting compound or intermediate and reacting the compound or intermediate with one or more chemical reagents in one or more steps to produce a compound described herein or illustrated in the accompanying figures.

Some of the compounds described herein can be obtained from commercial sources. As noted, others can be synthesized by conventional methods using commercially available starting materials and reagents. The compounds described herein can be separated from a reaction mixture and further purified by a method such as column chromatography, high-pressure liquid chromatography, or recrystallization. As can be appreciated by one of ordinary skill in the art, further methods of synthesizing the compounds of the formulae herein are available. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in Larock, *Comprehensive Organic Transformations*, VCH Publishers, 1989; Greene and Wuts, *Protective Groups in Organic Synthesis*, 2d. Ed., John Wiley and Sons, 1991; Fieser and Fieser, *Fieser and Fieser's Reagents for Organic Synthesis*, John Wiley and Sons, 1994; and Paquette, ed., *Encyclopedia of Reagents for Organic Synthesis*, John Wiley and Sons, 1995, and subsequent editions thereof. Techniques useful for the separation of isomers, for example, stereoisomers are within skill of the art and are described in Eliel et al., *Stereochemistry of Organic Compounds*, Wiley Interscience, NY, 1994. For example compounds can be resolved via formation of diasteromeric salts, for example, with a chiral base, for example, (+) or (−) a-methylbenzylamine, or via high performance liquid chromatography using a chiral column.

Platform and scaffold use: In an alternate embodiment, the compounds described herein may be used as platforms or scaffolds that may be utilized in combinatorial chemistry techniques for preparation of dervatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., "Solid-Supported Combinatorial and Parallel Synthesis of Small-Molecular-Weight Compound Libraries", Pergamon-Elsevier Science Limited (1998), and include those such as the "split and pool" or "parallel" synthesis techniques, solid-phase and solution-phase techniques, and encoding techniques (see, for example, Czarnik, *Curr. Opin. Chem. Bio.* 1:60, 1997). Thus, one embodiment relates to methods of using the compounds described herein for generating derivatives or chemical libraries. The methods can be carried out by performing these, and optionally additional, steps: (1) providing a body comprising a plurality of wells; (2) providing one or more compounds identified by methods described herein in each well (e.g., any of the compounds of Formulas I-X; (3) providing an additional one or more chemicals in each well, where the compound, upon exposure to the chemical(s) may produce one or more products; and (4) isolating the resulting one or more products from each well. We may refer to the original compound as the "first" compound and to the chemical as the "second" compound. The order in which the first and second compounds are added to the wells can vary, and the methods can be carried out in vitro or in cell culture. Lead derivatives can be further tested in animal models.

In alternate embodiments, the methods of using the compounds described herein for generating derivatives or chemical libraries can be carried out using a solid support. These methods can be carried out by, for example: (1) providing one or more of the compounds described herein attached to a solid support; (2) treating the one or more compounds identified by methods described herein attached to a solid support with one or more additional compounds or chemicals; (3) isolating the resulting one or more products from the solid support. In these methods, "tags" or identifier or labeling moieties may be attached to and/or detached from the compounds described herein or their derivatives, to facilitate tracking, identification or isolation of the desired products or their intermediates. Such moieties are known in the art and exemplary tags are noted above. The chemicals (or "second" compound(s)) used in the aforementioned methods may include, for example, solvents, reagents, catalysts, protecting group and deprotecting group reagents, and the like. Examples of such chemicals are those that appear in the various synthetic and protecting group chemistry texts and treatises which are known in the art and may be referenced herein.

Databases: In one aspect, the invention includes cell-based and in vitro assays (e.g., high throughput screens) that can be used with essentially any compound collection. Following an assay, the result can be recorded in a database, and such databases are also within the scope of the present invention. For example, the invention features a computer-readable database that includes a plurality of records. Each record includes (a) a first field that includes information reflecting the identity of an agent (e.g., an agent within one of the types of libraries described herein) and (b) a second field that includes information concerning the impact of the agent on polypeptide association. Additional fields may include the results of toxicity tests, dose-response tests, and the like. The information contained with the fields can be obtained in any order (e.g., the information reflecting protein association can be obtained first). However, to help ensure the integrity of the database, the information should be obtained independently (or "blindly"). The database can also include a field comparing the agent to a clinical outcome (e.g., an improvement in a sign or symptom associated with Parkinson's disease, Huntington's disease, cancer, or any of the other disorders described herein). The number of records can be, but is not necessarily, great. For example, a useful database can include at least 10, 25, 50, 100, 250, 500, 1000, 1500, 1800, 2000, or 2500 records.

The invention is further illustrated by the following examples, which should not be construed as further limiting.

EXAMPLES

The studies that follow demonstrate, inter alia, that inhibiting SIRT2 deacetylase activity can reduce α-synuclein toxicity and promote aggregate enlargement in a cellular model of Parkinson's Disease.

The pathological mechanisms that cause neurodegeneration in Parkinson's disease (PD) remain elusive. This incomplete understanding, together with apparent disease heterogeneity, makes it difficult to identify useful molecular targets for drug treatment. In some instances, Parkinson's Disease is caused by a genetic defect in which the wild type α-synuclein allele is multiplied, and this form of the disease has been recapitulated in cell culture, where transient overexpression of α-synuclein results in cellular toxicity. Here, we show that inhibition of human SIRT2 activity rescues α-synuclein-dependent cell-death. We discovered weak but selective SIRT2 inhibitory activity with a previously identified compound, and this prompted us to further investigate the target for this compound. We observed that SIRT2, but not SIRT3, siRNA prevented α-synuclein cell-death as well. For several reasons, including further investigation of the efficacy of SIRT2 inhibition in this PD model, we developed a potent and selective SIRT2 inhibitor. This compound was capable of preventing cellular α-synuclein toxicity in a dose-dependent manner. The inhibitor-dependent cell rescue was associated with changes in aggregation phenotype; small aggregates coalesced into a few large inclusions. Our data implicate a protein's acetylation status as an important factor contributing to neurodegeneration and suggest therapeutic intervention in PD by pharmacological inhibition of SIRT2 with new small molecule inhibitors.

Plasmid construction: The constructs for human wild type α-synuclein and its C-terminal tagged version (referred to as synT) have been described previously (McLean et al., *Neuroscience* 104:901-912, 2001; McLean et al., *J. Neurochem.* 83:846-854, 2002). In order to amplify the full length SIRT2 gene, a truncated clone was purchased from the Mammalian Gene Collection (Invitrogen, Carlsbad Calif., clone number 2820929) and extended in a stepwise fashion with three successive PCR reactions to obtain the full-length product. In the final amplification step, primers containing restriction enzyme sites and a C-terminal myc tag were added onto the ends of the SIRT2 gene and cloned into a pcDNA3.1hygro vector (Invitrogen). All cloning was sequence verified.

Cell culture and transfection: HeLa cells were cultured in DMEM supplemented with 10% fetal bovine serum (FBS) and 2 mM L-glutamine. Human H4 neuroglioma cells ("H4 cells" HTB-148 from the American Type Culture Collection (ATCC), Manassas, Va., USA) were maintained in OPTI-MEM (Life Technologies, Grand Island, N.Y., USA) supplemented with 10% FBS. H4 cells were passaged 24 hours prior to transfection and plated in 24-well plates. The cells were transfected, using a pcDNA3.1hygro vector (Invitrogen) and SUPERFECT (Qiagen, Chatsworth, Calif., USA) according to the manufacturer's instructions. Compounds or DMSO were added after the transfection procedure was concluded.

For the immunoblotting experiments, cells were plated in 60 mm dishes 24 hours prior to transfection. Transfections were performed as described above.

α-Synuclein toxicity assay: Toxicity was analyzed 24 hours after transfection by measuring the release of adenyate kinase from damaged cells into the culture medium using the ToxiLight™ kit (Cambrex, Walkersville, Md.) according to the manufacturer's protocol.

SDS-PAGE and immunoblotting: 24 hours after transfection, H4 cells were washed with cold PBS, harvested by scraping in cold lysis buffer without detergents (Tris/HCl 50 mM pH 7.4, NaCl 175 mM, EDTA 5 mM pH 8.0, protease inhibitor cocktail (Roche, Basel, CH) and sonicated for 10 seconds. Protein concentration was estimated using the BCA method, and the appropriate volume of each sample was diluted in 4×SDS sample buffer. Lysates were subjected to SDS-PAGE using 10-20% Tris-Glycine gels (Novex, San Diego, Calif., USA) for Western blot analysis. Protein was transferred to Immobilon-P membrane (Millipore, Bedford, Mass., USA) and blocked in blocking buffer (Lycor, Lincoln, Nebr., USA) for 1 hour prior to the addition of the primary antibody (anti-Hsp70 and anti-Hsp27 were obtained from Stressgen; anti-DJ-1 was obtained from Chemicon, anti-α-synuelein—syn1, BD, and anti-actin were obtained from Sigma) at room temperature for 1-2 hours or overnight at 4° C. The blots were washed three times in Tris-buffered saline with 0.2% Tween (TBS-T, pH 7.4) and were incubated at room temperature for 1 hour in fluorescent labeled secondary antibodies (IRDye 800 anti-rabbit or anti-mouse, Rockland Immunochemicals, Gilbertsville, Pa., USA, 1:3000 or Alexa-680 anti-rabbit or anti-mouse, Molecular Probes, Eugene, Oreg., USA 1:3000). After three washes in TBS-T, immunoblots were processed and quantified using the Odyssey infrared imaging system (Lycor, Lincoln, Nebr., USA).

Tubulin and sirtuin Western blot analysis: Samples were separated on 10% polyacrylamide gels and transferred to a 0.45 μm PVDF membrane (Millipore, Bedford Mass.). Membranes were blocked with a 5% milk solution in PBST. Blots were then probed with antibodies to either SIRT2 (Santa Cruz A-5 at 1:100), tubulin (Sigma, St. Louis Mo., B-5-1-2) or acetylated tubulin (Sigma, 6-11B-1), both at 1:5000. Secondary detection was performed using an HRP-conjugated anti-mouse antibody (Sigma) at 1:4000, and exposed using an ECL detection kit (PerkinElmer).

Immunoprecipitations: For the immunoprecipitation experiments, HeLa cells were plated to 90% confluence in antibiotic free medium and allowed to attach overnight. The next morning, medium was removed and replaced with the SIRT2 DNA construct complexed with Lipofectamine 2000 (Invitrogen) diluted in Opti-MEM (Gibco). After 4 hours, complete culture medium was added and cells were incubated for 24 hours. Cells were then collected by treatment with trypsin and centrifuged at 500×g for 5 minutes. The resulting cell pellet was washed once with PBS, then lysed in immunoprecipitation buffer (50 mM Tris-HCl pH 7.5, 150 mM NaCl, 1% NP40, 0.5% sodium deoxycholate 25× protease inhibitor cocktail, and 0.7 µg/mL pepstatin) for 10 minutes on ice with occasional vortexing. Cell extracts were cleared by centrifugation at 10,000×g for 10 min, and the supernatant was removed to a clean tube. Immunoprecipitation was carried out by first preclearing the lysate with 50 µL of protein G conjugated agarose beads for 1 hour at 4° C. After the preclearing step, beads were sedimented and the supernatant removed to a clean tube. Next, 2 µg of anti-c-myc antibody (Santa Cruz, La Jolla Calif., 9E10) was added for 1 hour at 4° C., followed by protein G agarose beads for 2 hours, after which the beads were allowed to sediment. Beads were washed 2×10 minutes in both a high salt (500 mM NaCl) and low salt (no NaCl) buffer, followed by a 10 minute wash in SIRT buffer (50 mM Tris-HCl pH 8.0, 137 mM NaCl, 2.7 mM KCl, 1 mM $MgCl_2$ and 1 mg/mL BSA). Upon removal of the last wash, SIRT2 conjugated beads were resuspended in SIRT buffer and used immediately.

Fluorescent SIRT enzyme assay: Recombinant SIRT enzymes and fluorescent peptide substrates were purchased from Biomol (Plymouth Meeting, Pa.) and used according to the manufacturer's instructions. Briefly, substrate was added to a final concentration of 50 µM, supplemented with 500 µM $NAD^+$. Compounds were then added to the appropriate wells, with controls receiving DMSO only. Finally, enzyme was added and the reaction allowed to proceed for 1 hour at 37° C., at which time a developer solution was added and the samples read at 355/460 nm. For the enzyme immunoprecipitation experiments, the procedure was the same as above except immunoprecipitated enzyme was used in place of recombinant enzyme.

Tubulin deacetylation reaction: To measure in vitro tubulin deacetylation, the fluorescence based SIRT enzyme assay was modified such that the fluorescent peptide substrate was replaced with 0.5 µg of purified tubulin heterodimers (Cytoskeleton, Denver Colo.). The reaction was allowed to proceed for 2 hours, at which time the reaction was terminated by addition of 3×SDS sample buffer. An aliquot was then loaded onto a 10% polyacrylamide gel and analyzed as described in the Western blotting section of the methods.

Cell-based SIRT2 inhibition: HeLa cells were plated to 75% confluency in a 24-well plate and allowed to attach overnight. The following morning, medium was removed and fresh medium containing compound was added to the wells. After 3 hours, medium was removed and cells were washed 3× with PBS. After the final wash, 100 µL of a hypotonic lysis buffer was added to each well, and the cells were lysed at 37° C. for 5 minutes. The lysates were transferred to eppendorf tubes and centrifuged at 16,000×g for 10 minutes at room temperature. The resulting supernatant contained soluble tubulin monomers, while the pellet contained the insoluble microtubule polymers. The supernatant was removed to a clean tube and 100 µL of hypotonic lysis buffer was used to resuspend the pellet. SDS sample buffer was added to all the samples, followed by Western blot analysis.

Figure 3:
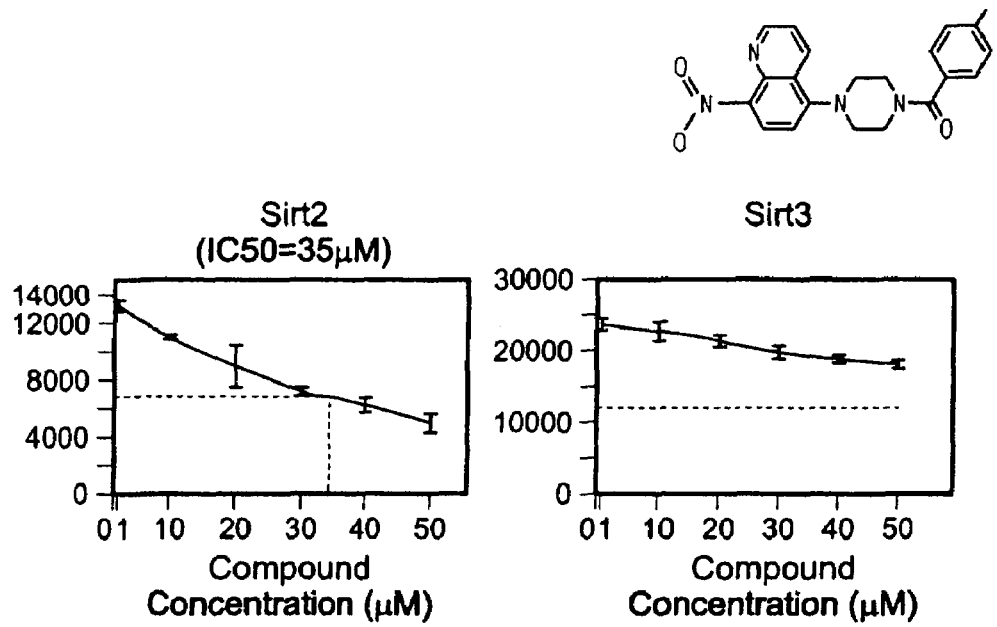
FIG. 3 is a schematic representation of the compound B2 and line graphs demonstrating its effect on SIRT2 and SIRT3 over concentrations of B2 ranging from 0.1 to 50 μM.

Identification of AGK2 as a SIRT2 inhibitor: We previously identified a compound referred to as B2 that inhibits α-synuclein-mediated cellular toxicity (B2 is compound E1 in WO 05/087217). The inhibition or cellular "rescue" is associated with a decrease in the number of small α-synuclein aggregates and the formation of large inclusions. Using a primary aggregation screening assay, we analyzed B2 analogs and demonstrated the specificity of this small molecule. As we have not yet been able to optimize potency to the extent desired, we also began to search for other compounds using a panel of selected biochemical assays. For assay selection, we took into consideration other activities of B2, including: rescue of proteasome dysfunction mediated by extended polyglutamines and the ability to increase the size of polyglutamine inclusions, a feature reminiscent of the phenotype of cells that overexpress α-synuclein. The phenotype exhibiting increased polyglutamine aggregation was observed in a primary assay in the presence of HDAc inhibitors against enzyme classes I and II, such as SCRIPTAID and TSA, respectively. B2 has been tested in cell-free enzymatic assays for activity against caspase 1, caspase 6, BACE1, calpain, cathepsins H, L, and S, HDAcs of class I and class II, and sirtuins of type 1, 2, and 3. Previously, B2 was tested for chaperone activity. The only detected activity was weak ($IC_{50}$=35 µM), but we did observe selective inhibition of SIRT2 (FIG. 3). The activity of B2 against recombinant SIRT2 and SIRT3 strengthened our belief that SIRT2 is a molecular target for the present compounds and that inhibition of SIRT2 modulates protein-protein aggregation in a beneficial way.

Figure 4:
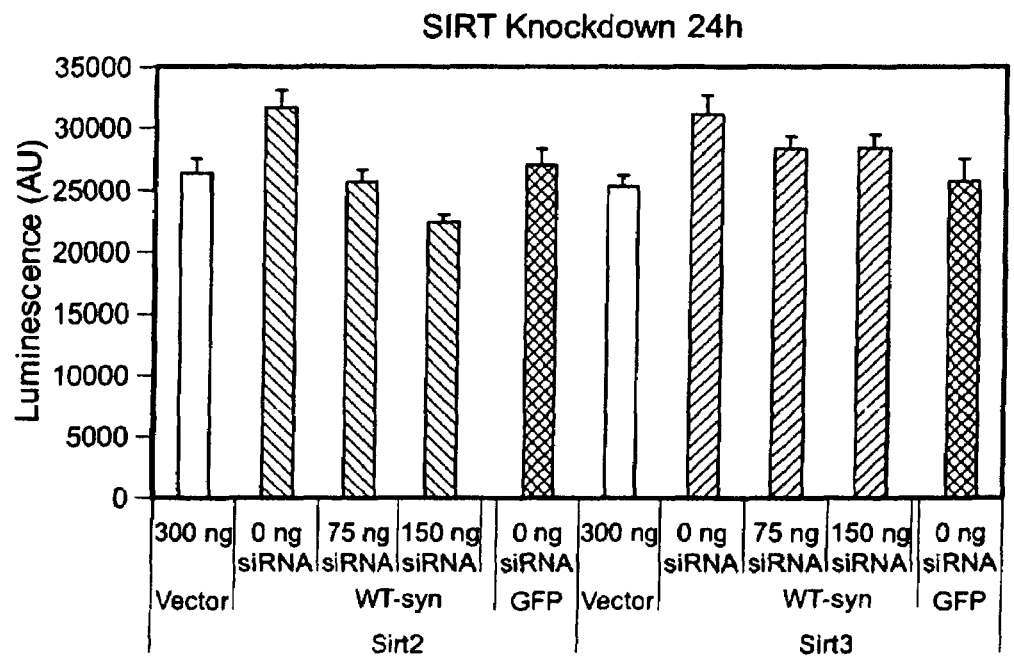
FIG. 4 is a bar graph representing the results of our studies with siRNA to inhibit SIRT2 and SIRT3.

Since B2 activity in vitro was quite weak, we used a genetic approach to further investigate the consequences of SIRT2 inhibition. The same H4 cells were transfected with α-synuclein expression constructs and synthetic siRNA against SIRT2 or SIRT3 mRNAs. We observed the rescue of α-synuclein toxicity only in cells receiving SIRT2 siRNA (FIG. 4). Unfortunately, in genetic experiments we were not able to correlate functional rescue with changes in aggregation. Thus, for further target validation, we employed a chemical approach to discover potent and selective small molecule inhibitors of SIRT2.

Figure 5A:
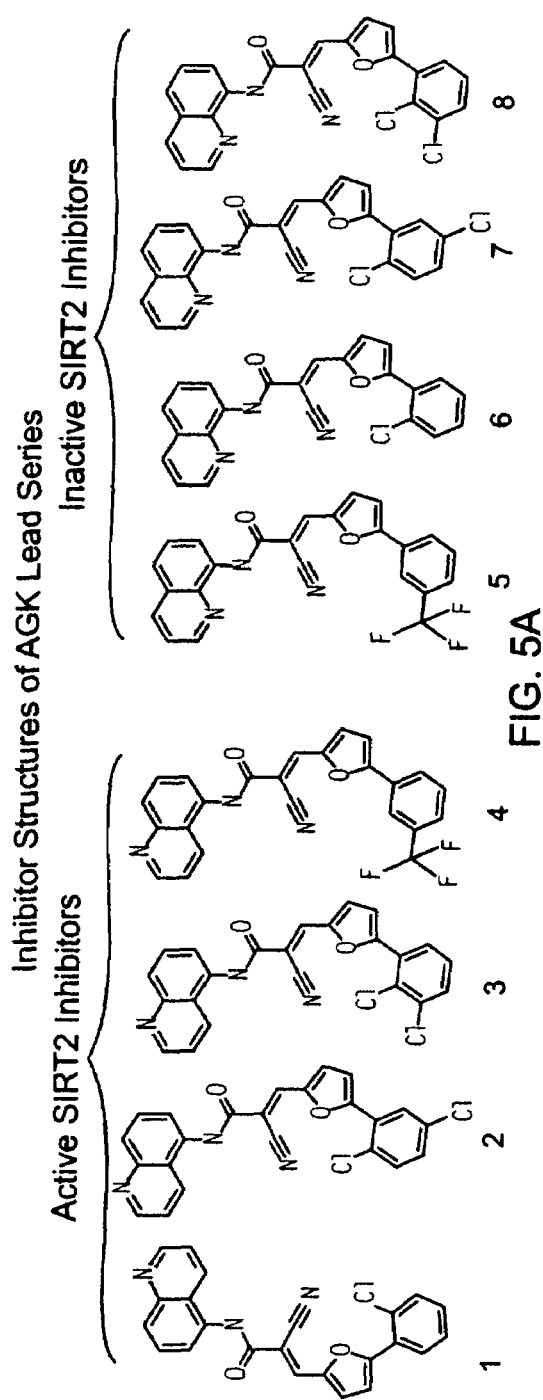
Figure 5B:
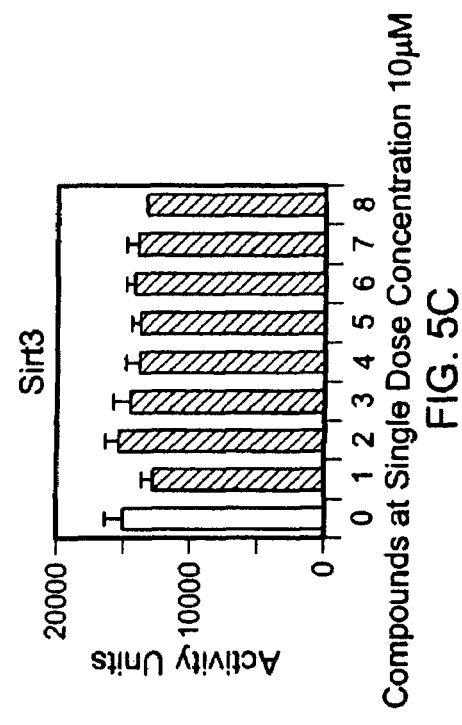
Figure 5C:
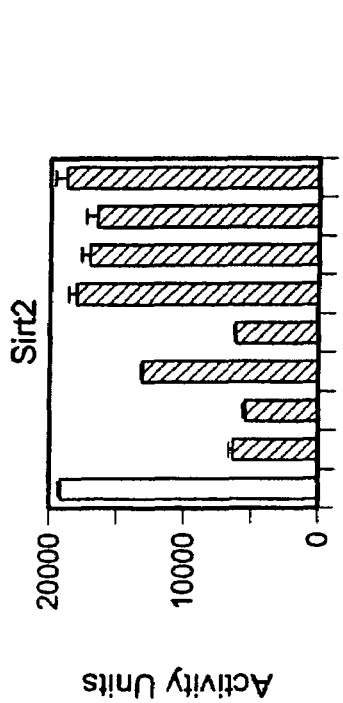
Figure 6A:
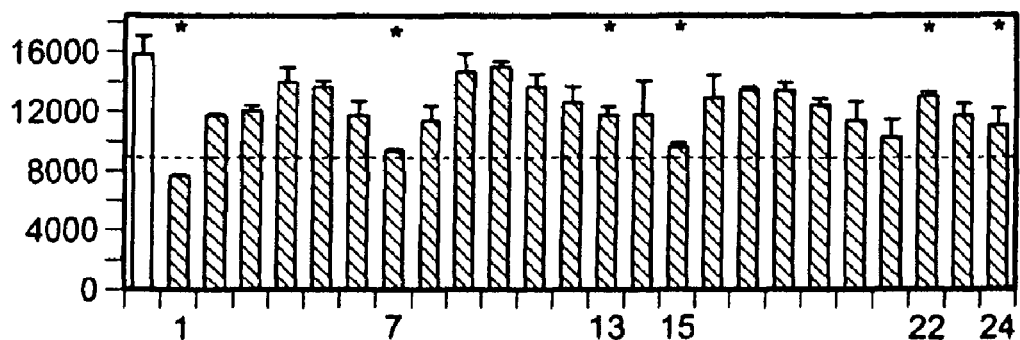
FIG. 6A is a bar graph representing the ability of compounds conforming to Formula III to inhibit SIRT2 activity. The unfilled bar represents SIRT2 activity in the absence of a potential inhibitory compound. Compounds AK-1, AK-7, AK-13, AK-15, AK-22, and AK-24, which are shown in FIG. 6D, were tested further at various concentrations from 6 to 50 μM (FIGS. 6B (SIRT2) and 6C (SIRT3)).
Figure 6B:
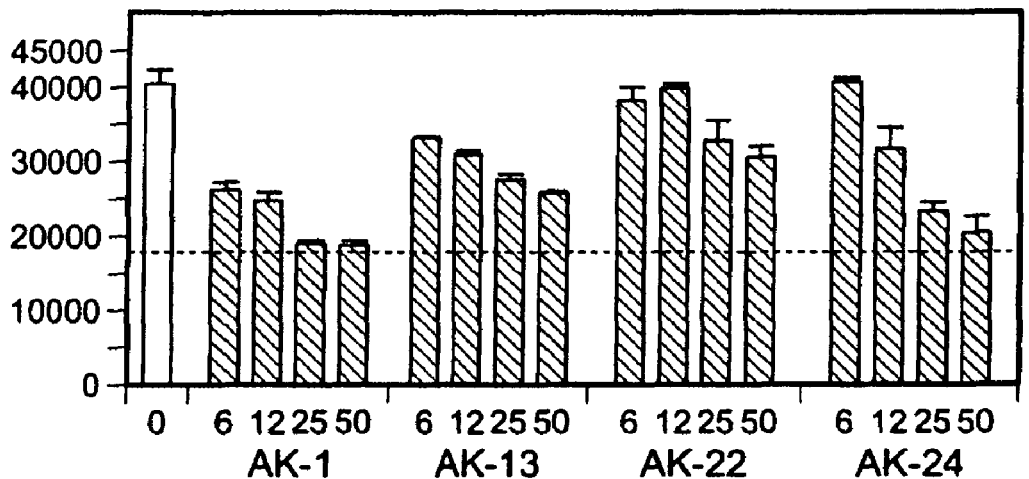
Figure 6C:
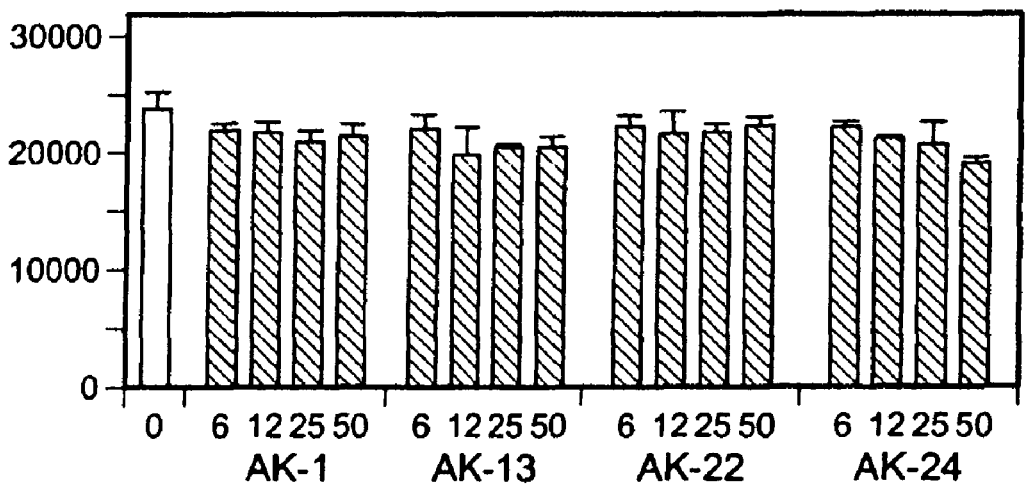
Figure 6D:
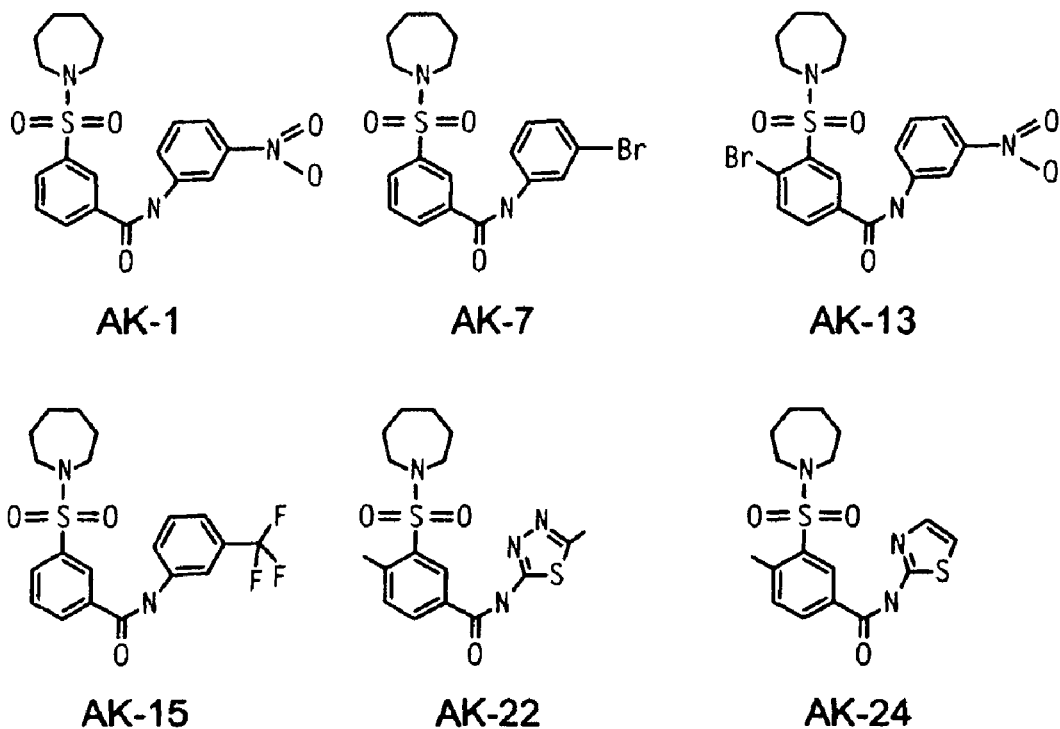

Using the structure of B2 as a starting point, we designed a focus library of B2 analogs. Using commercially available fluorometric SIRT enzyme assays, we screened a focus library of 200 compounds in search of a more potent SIRT2 inhibitor. The most promising lead from this screen was compound AGK2 (compound 2 of the 8 shown in FIG. 5A; see also FIGS. 5B-5C). An inhibition profile was generated for AGK2 against various sirtuins (FIG. 5D). The inhibition profile for SIRT2 shows a calculated $IC_{50}$ value of 3.5 µM, representing a 10-fold increase in potency of AGK2 over B2 (FIG. 5E). To determine the relative selectivity of AGK2 for SIRT2, we tested this compound against SIRT1 and SIRT3. AGK2 slightly inhibits SIRT1 and SIRT3 at compound concentrations of 40 µM or higher, demonstrating that AGK2 is indeed selective for SIRT2 (FIGS. 5F and 5G, respectively).

We also designed focus libraries based on structural similarity to previously identified compounds that modified intracellular polyglutamine aggregation. Using biochemical assays, we have identified additional inhibitors that are also selective for SIRT2 but less potent than AGK2 (FIGS. 6A-6D).

Figure 7:
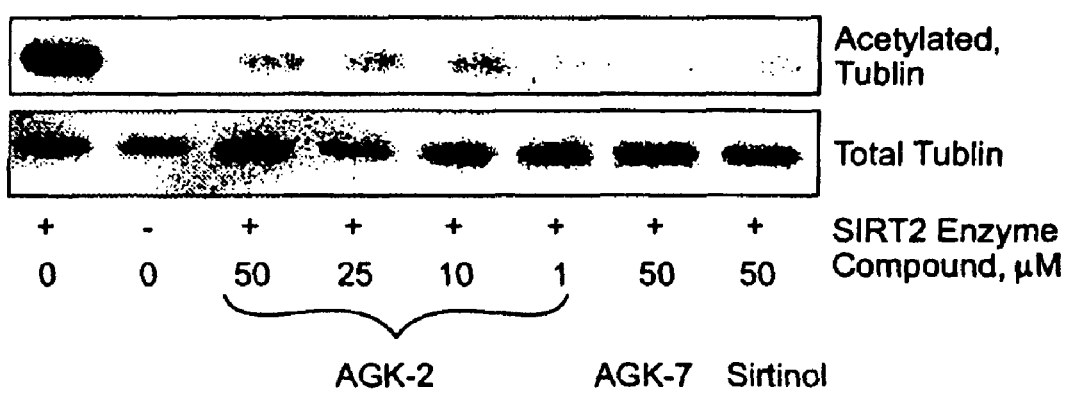
FIG. 7 is a photograph of a Western blot. The top row shows the levels of expression of acetylated tubulin in the conditions indicated under each lane, including expression levels in the presence of varying amounts (μM) of AGE2, AGK7, and SIRTINOL. The bottom row shows the levels of expression of total tubulin in the conditions indicated. Recombinant SIRT2 was mixed with alpha tubulin in the presence or absence of compound. After 2 hours, the samples were subjected to Western analysis with acetylated and total tubulin antibodies.

Validation of SIRT2 inhibition by AGK2: After demonstrating the activity of AGK2 using an artificial fluorescent substrate, we wanted to determine whether AGK2 could inhibit the activity of SIRT2 against a native substrate. As noted above, North et al. have shown that SIRT2 can deacetylate the lysine at position 40 of alpha tubulin, both in purified tubulin heterodimers, and in taxol-stabilized microtubules. Accordingly, we substituted the artificial peptide substrate for tubulin heterodimers purified from bovine brain, which is a rich source of acetylated tubulin. Treatment with AGK2 led to an increase in acetylated tubulin over both the inactive compound control as well as the known SIRT2 inhibitor SIRTINOL (FIG. 7).

We next wanted to determine whether AGK2 was active against SIRT2 that had been expressed from a recombinant construct in mammalian cells. To accomplish this, we generated a full-length clone of SIRT2 fused to a C-terminal myc tag. This construct was transfected into HeLa cells and immunoprecipitated at 48 hr using an anti C-myc antibody. The immunoprecipitated SIRT2 was used in place of recombinant SIRT2 in the above mentioned fluorescent enzyme assay, and treated with or without ASK2. AGK2 was also able to inhibit SIRT2 that had been folded and processed by the intracellular machinery. We found that AGC was not active against SIRT3 generated in the same manner.

In other studies, we used the techniques of computational chemistry to design a three-dimensional structure of the SIRT2 active site and docked active inhibitors. Consistent with docking data were results from competition experiments. AIK2 weakly competed with the co-factor NAD+ and showed no competition with protein substrates.

Remarks: The studies described above indicate that AGK2 can rescue α-synuclein toxicity. Functional rescue was correlated with formation of large inclusions, while reducing number of small aggregates in cells. The SIRT2 inhibitor AK-1 prevented some α-synuclein toxicity as well and mediated cell rescue in accordance with increased inclusion size (similar to effect of AGK2).

Following inhibition of SIRT2 activity in vitro we identified selective and potent small molecule inhibitors as exemplified by AGK2. This Inhibitor was bio-active, increasing the acetylation of α-tubulin in compound-treated cells. Using a developed small molecule, we demonstrated efficacy of SIRT2 inhibition in an α-synuclein toxicity assay. Functional rescue was correlated with a reduced number of multiple α-synuclein aggregates and marked formation of large inclusions. It is conceivable that the state of α-synuclein aggregates determines its toxic cellular function and that there is a benefit to reducing the total surface area of the aggregates (as occurs when they coalesce into large inclusions). It is also possible that increased aggregation reduces the concentration of sub-microscopic toxic species (e.g., oligomers) and thus lowers the burden on the cell and cellular organelles such as proteasomes.

Inhibition of SIRT2 activity caused an elevation of α-tubulin acetylation, which leads to microtubule stabilization. According to published data, α-synuclein interacts with α-tubulin and may destabilize microtubules. We have not observed effects of mutant or wild-type α-synuclein on tubulin polymerization/de-polymerization in vitro or detected protein interactions by immunoprecipitations. Nevertheless, α-synuclein invasion of microtubules leading to cytoskeleton destabilization may take place in vivo. Similarly, increased levels of acetylated α-tubulin molecules, readily polymerized, may directly or indirectly stimulate aggregation of α-synuclein.

It is possible that increased acetylation of other SIRT2 substrates, affecting gene transcription or protein turnover, are involved in amelioration α-synuclein toxicity. We have not yet observed an increase in transcription in the presence of SIRT2 inhibitors, nor have we have detected changes in α-synuclein expression levels. Nevertheless, efficacy of SIRT2 inhibition in Parkinson's Disease assay may be depend on cellular pathways, triggered by increase acetylation of p53 or H4.

OTHER EMBODIMENTS

A number of embodiments of the invention have been described. Nevertheless, it will be understood that various modifications may be made without departing from the spirit and scope of the invention. Accordingly, other embodiments are within the scope of the following claims,

What is claimed is:

1. A compound of Formula I:

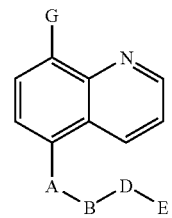

or a pharmaceutically acceptable salt thereof, wherein
A is S;
B is triazole optionally substituted by phenyl;
D is CH—O;
E is phenyl optionally substituted by 1 2, 3, or 4 substituents independently selected from halo, OH, CN, and $C_{1-6}$ akyl;
G is H, $NR^4R^5$, or $NO_2$;
$R^4$ and $R^5$ are independently selected from H, $C_{1-6}$ alkyl, and $C_{1-6}$ haloalkyl.

2. The compound of claim 1, wherein the E is substituted with at least one halo.

3. The compound of claim 1, wherein the E is substituted with two halo.

4. The compound of claim 3, wherein the halo are chloro.

5. A pharmaceutical composition comprising the compound of claim 1.

6. The compound of claim 1, wherein G is $NO_2$.

7. The compound of claim 1, wherein B is substituted with phenyl.

8. The compound of claim 1, wherein the compound is:

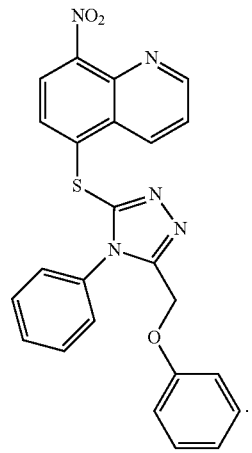

9. A pharmaceutical composition comprising the compound of claim 8.

* * * * *